(12) United States Patent
Costello

(10) Patent No.: US 7,837,634 B2
(45) Date of Patent: Nov. 23, 2010

(54) FIBEROPTIC TISSUE MOTION SENSOR

(75) Inventor: Benedict James Costello, Berkeley, CA (US)

(73) Assignee: Proteus Biomedical, Inc., Redwood City, CA (US)

( * ) Notice: Subject to any disclaimer, the term of this patent is extended or adjusted under 35 U.S.C. 154(b) by 603 days.

(21) Appl. No.: 11/368,259

(22) Filed: Mar. 3, 2006

(65) Prior Publication Data

US 2006/0217793 A1    Sep. 28, 2006

Related U.S. Application Data

(60) Provisional application No. 60/658,445, filed on Mar. 3, 2005.

(51) Int. Cl.
| | |
|---|---|
| A61B 5/103 | (2006.01) |
| A61B 5/117 | (2006.01) |
| F21V 9/00 | (2006.01) |
| G02B 6/26 | (2006.01) |
| G02B 6/42 | (2006.01) |

(52) U.S. Cl. .......................... 600/595; 362/511; 385/15
(58) Field of Classification Search ................. 600/595; 362/511; 385/15
See application file for complete search history.

(56) References Cited

U.S. PATENT DOCUMENTS

| | | | | | |
|---|---|---|---|---|---|
| 4,945,916 | A | * | 8/1990 | Kretschmer et al. | 600/484 |
| 5,127,269 | A | * | 7/1992 | Grudzien, Jr. | 73/705 |
| 5,146,091 | A | * | 9/1992 | Knudson | 250/341.6 |
| 5,202,939 | A | * | 4/1993 | Belleville et al. | 385/12 |
| 5,268,977 | A | * | 12/1993 | Miller | 385/33 |
| 5,298,741 | A | * | 3/1994 | Walt et al. | 250/227.23 |
| 5,629,790 | A | * | 5/1997 | Neukermans et al. | 359/198 |
| 5,991,661 | A | | 11/1999 | Park et al. | |
| 6,002,963 | A | | 12/1999 | Mouchawar et al. | |
| 6,019,736 | A | * | 2/2000 | Avellanet et al. | 600/585 |
| 6,031,946 | A | * | 2/2000 | Bergmann et al. | 385/18 |
| 6,044,299 | A | | 3/2000 | Nilsson | |
| 6,058,329 | A | | 5/2000 | Salo et al. | |
| 6,077,136 | A | | 6/2000 | Arai et al. | |
| 6,216,022 | B1 | * | 4/2001 | Tyrrell et al. | 600/310 |

(Continued)

FOREIGN PATENT DOCUMENTS

WO    WO 2004/066825    8/2004

OTHER PUBLICATIONS

STIC Searches—Two (2) Documents, Perfromed by Jeanne Horrigan.*

(Continued)

*Primary Examiner*—Max Hindenburg
*Assistant Examiner*—Sean P Dougherty
(74) *Attorney, Agent, or Firm*—Bret E. Field; Bozicevic, Field & Francis LLP

(57) ABSTRACT

Devices and methods for evaluating motion of a tissue location, such as cardiac tissue location, e.g., heart wall, are provided. Devices employed in the subject methods are fiberoptic tissue motion sensors that include a light guide having a reflective element at its distal end and a light emitter/detector at its proximal end. In embodiments of the methods, a signal obtained from reflective element stably associated with the tissue location of interest is employed to evaluate movement of the tissue location. The subject methods and devices find use in a variety of different applications, including cardiac resynchronization therapy.

22 Claims, 16 Drawing Sheets

U.S. PATENT DOCUMENTS

| | | |
|---|---|---|
| 6,353,692 B1 * | 3/2002 | Colbourne .................... 385/16 |
| 6,366,811 B1 | 4/2002 | Carlson |
| 6,625,493 B2 | 9/2003 | Kroll et al. |
| 6,628,856 B1 * | 9/2003 | Costello et al. ............... 385/18 |
| 2003/0105496 A1 | 6/2003 | Yu et al. |
| 2004/0199223 A1 * | 10/2004 | Andersen et al. .............. 607/89 |
| 2005/0192591 A1 * | 9/2005 | Lui et al. .................... 606/108 |

OTHER PUBLICATIONS

A. Kloppe, et al, Mechanical and optical characteristics of a new fiber optical system used for cardiac contraction measurement, Medical Engineering & Physics 26 (2004) 687-694.*

* cited by examiner

FIBEROPTIC TISSUE MOTION SENSOR

CROSS-REFERENCE TO RELATED APPLICATION

Pursuant to 35 U.S.C. §119 (e), this application claims priority to the filing date of: U.S. Provisional Patent Application Ser. No. 60/658,445 filed Mar. 3, 2005; the disclosure of which is herein incorporated by reference.

BACKGROUND

The present Invention relates generally to medical apparatus and methods. More specifically, the invention relates to apparatus and methods for optimizing cardiac resynchronization intervention, arrhythmia management, ischemia ejection, coronary artery disease management, and heart failure management.

Cardiac resynchronization therapy (CRT) is an important new medical intervention for patients suffering from congestive heart failure. When congestive heart failure occurs, symptoms develop due to the heart's inability to function sufficiently well as a mechanical pump to supply the body's physiological needs. Congestive heart failure is characterized by gradual decline in cardiac function punctuated by severe exacerbations leading eventually to death. It is estimated that over five million patients in the United States suffer from this malady.

The aim of resynchronization pacing is to induce the interventricular septum and the left ventricular free wall to contract at approximately the same time.

Resynchronization therapy seeks to provide a contraction time sequence which will most effectively produce maximal cardiac output with minimal total energy expenditure by the heart. The optimal timing is calculated by reference to hemodynamic parameters such as dP/dt, the first time-derivative of the pressure waveform in the left ventricle. The dP/dt parameter is a well-documented proxy for left ventricular contractility.

In current practice, external ultrasound measurements are used to calculate dP/dt. Such external ultrasound is used to observe wall motion directly. Most commonly, the ultrasound operator uses the ultrasound system in a tissue Doppler mode, a feature known as tissue Doppler imaging or TDI, to evaluate the time course of displacement of the septum relative to the left ventricle free wall. The current view of clinicians is that ultrasonographic evaluation using TDI or a similar approach may become an important part of qualifying patients for CRT therapy.

As currently delivered, CRT therapy is effective in about half to two-thirds of patients implanted with a resynchronization device. In approximately one third of these patients, this therapy provides a two-class improvement in patient symptoms as measured by the New York Heart Association fair level scale. In about one third of these patients, a one-class improvement in cardiovascular symptoms is accomplished. In the remaining third of patients, there is no improvement or, in a small minority, a deterioration in cardiac performance. This group of patients is referred to as non-responders. It is possible that the one-class New York Heart Association responders are actually marginal or partial responders to the therapy, given the dramatic results seen in a minority.

The synchronization therapy, in order to be optimal, targets the cardiac wall segment point of maximal delay, and advances the timing to synchronize contraction with an earlier contracting region of the heart, typically the septum. However, the current placement technique for CRT devices is usually empiric. A physician will cannulate a vein that appears to be in the region described by the literature as most effective. The device is then positioned, stimulation is carried out, and the lack of extra cardiac stimulation, such as diaphragmatic pacing, is confirmed. With the currently available techniques, rarely is there time or means for optimizing cardiac performance.

When attempted today, CRT optimization must be performed by laborious manual method of an ultrasonographer evaluating cardiac wall motion at different lead positions and different interventricular delay (IVD) settings. The IVD is the ability of pacemakers to be set up with different timing on the pacing pulse that goes to the right ventricle versus the left ventricle. In addition, all pacemakers have the ability to vary the atrio-ventricular delay, which is the delay between stimulation of the atria and the ventricle or ventricles themselves. These settings can be important in addition to the location of the left ventricular stimulating electrode is itself in resynchronizing the patient.

Some research efforts to assess cardiac motion through internal accelerometry signals have been made. For example, researchers have described the use of epicardial accelerometry for detecting arrhythmia. Kroll et al. teach a positional accelerometer for rate control (U.S. Pat. No. 6,625,493, issued Sep. 23, 2003). Mouchawar et al. disclose cardiac wall motion detection using an accelerometer for detection of arrhythmias (U.S. Pat. No. 6,002,963, issued Dec. 14, 1999). Park et al. teach the use of an accelerometer for rate adaptive pacing (U.S. Pat. No. 5,991,661, issued Nov. 23, 1999). Nilsson describes an in-can accelerometer to provide rate control (U.S. Pat. No. 6,044,299, issued Mar. 28, 2000).

Other research groups have explored the use of accelerometry in cardiac applications. Carlson et al. teach the use of an in-can accelerometer which derives pulse pressure for pacing (CRT) optimization using signals from an accelerometer and an ECG (U.S. Pat. No. 6,366,811, issued Apr. 2, 2002). Salo et al. teach the use of an accelerometer with signal processing circuitry to measure total acoustic notes to optimized CRT (U.S. Pat. No. 6,058,329, issued May 2, 2000). Cunningham teaches use of an accelerometer in the ventricle on a lead to monitor cardiac contractility (U.S. Pat. No. 6,077,136, issued Jun. 20, 2000).

Furthermore, current accelerometry in cardiac applications include implantable accelerometers for determining patient activity levels. With these devices, the pacemaker paced rate can adjust itself to allow for exercise and greater physical activity on the part of a pacemaker-dependent patient.

Recently, Overall et al. have described the concept of using apical accelerometry and other sensors to detect heart ischemia by detecting abnormalities in motion (WO 2004/066825 A2, published Aug. 12, 2004). Yu et al. have described the use of one-axis accelerometers alone to note difference in the synchronicity of ventricular wall location contractions (US 2003/0105496 A1, published Jun. 5, 2003).

Some researchers have reported the use of position sensors deployed along different aspects of the heart. Such sensors may be used to describe the extent of myocardial contraction and to effectively duplicate in part the function of ultrasonography. The parameters reported by such sensors include ejection fraction, stroke volume, cardiac output, and synchronization index. These systems typically adopt a fixed frame of reference using ultrasonographic, magnetic, or RF fields in orthogonal planes to generate a signal which can localize a catheter or catheters within the heart.

A challenge in seismocardiography is to reduce the form factor of the motion sensor which is typically implanted in a patient's heart. Conventional motion sensors and accelerometers typically have relatively large sizes. Consequently, the procedure involved in the insertion of such sensors into a patient's heart can be complex and invasive. Often, insertion of such devices, especially on a permanent basis, is impractical.

An apparatus for providing tissue movement assessment, e.g., in the form of cardiac wall timing, with a small form factor and a less invasive method of implanting such an apparatus, e.g., into a patient's heart, would be an important advancement in the art. A system for monitoring the mechanical performance of the heart in real time would have important clinical applications, such as in setting the functions of cardiac resynchronization therapy pacemakers, pharmacologic management of heart failure patients, arrhythmia detection, and ischemia detection.

SUMMARY

Devices and methods for evaluating motion of a tissue location, such as cardiac tissue location, e.g., heart wall, are provided. Devices employed in the subject methods are fiberoptic tissue motion sensors that include a light guide having a reflective element at its distal end and a light emitter and detector at its proximal end. In embodiments of the methods, a signal including timing thereof, obtained from reflective element stably associated with the tissue location of interest is employed to evaluate movement of the tissue location. The subject methods and devices find use in a variety of different applications, including cardiac resynchronization therapy.

The inventive fiberoptic cardiac wall motion timer provided herein enables, for the first time, a significantly smaller device to optimize cardiac resynchronization. The inventive device is considerably smaller than sensors previously used to measure cardiac motion, but with equal or greater sensitivity. By detecting changes in optical signals instead of electrical signals, and by combining fiberoptics and micro-machining technologies, the inventive fiberoptic cardiac wall motion timer provides a powerful new tool in a physician's armamentarium. This new tool facilitates accurate, real-time monitoring of heart wall timing, and thus performance.

Seismocardiography as practiced in the present invention, is a technique for recording cardiac vibrations limited to contraction timing. To perform this seismocardiography, one may place one or more of the inventive motion sensors inside a patient's heart and record the cardiac contraction as a function of time.

One of the immediate and particularly important applications for the inventive technological breakthrough of the invention is the use of the inventive fiberoptic cardiac wall motion timer to obtain optimal function settings for Cardiac Resynchronization Therapy (CRT). Employing the more basic embodiments of the present invention, a physician can accomplish optimal cardiac synchronization on a manual basis. The inventive cardiac wall motion timing technology can significantly reduce the prior available size of seismocardiography and other motion sensors. Consequently, the implantation procedures based on embodiments of the present invention are much less invasive than those based on prior technologies. Additionally, in more complex embodiments, the inventive fiberoptic cardiac wall motion timers provide cardiac motion data useful in the setting of CRT pacemakers, including automatic control mechanisms.

In general, when congestive heart failure occurs, portions of the heart become uncoordinated. The goal of cardiac resynchronization therapy is to induce various chambers of the heart to contract in a coordinated fashion and to maximize the efficiency of the pumping of blood. In a CRT procedure, electrodes are placed in a variety of locations inside the heart. These electrodes bring timed excitations to different portions of the heart to ensure that the heart beats in synchrony.

During a cardiac resynchronization process, it is important to monitor a number of parameters related to the cardiac motions. An ideal method is to physically measure the movement of specific portions of the heart. In this way, the clinician can determine the mechanical delay between motions of various portions of the heart. For instance, the clinician may be able to determine that the left ventricular free wall is contracting before or after the contraction of the ventricular septum.

Among different technologies for monitoring cardiac parameters, seismocardiography provides unique advantages because of its capability of providing precise, real-time data which can be used to analyze signals which cannot be distinguished by simple observation The present inventive fiberoptic cardiac wall motion timing technology allows unprecedented reduction of the size of a timer. It is very useful to minimize the size of a cardiac wall motion timer, in order to allow placement in optimal positions within the heart and limit procedure time. With a significantly reduced form factor, the present inventive fiberoptic cardiac wall motion timer can be implanted more easily, and the implantation procedure is much less invasive to the patient. As a result, the risks associated with the implantation procedure and the subsequent monitoring of cardiac motions is considerably lower.

Because of the small size of the present inventive fiberoptic cardiac wall motion timer, a physician can temporarily insert the timer within a guide wire lumen of a conventional cardiac pacing lead commonly used in CRT procedures. The benefit is that physicians will apply their knowledge of the existing pacemaker implantation procedure to perform a task which otherwise requires different, more complex procedures. Hence, patients can enjoy notably safer and more reliable CRT treatments.

One embodiment of the present invention provides a specific system that performs fiberoptic cardiac wall motion timing. The system includes a movable reflection element (i.e., mechanism) which is placed inside or external to a heart so that motion of the heart causes the reflection mechanism to move. The system further includes a light guide (i.e., light guiding mechanism) configured to direct light to, and collect light from the, reflection element. In this way, movement of the reflection element causes the amount of reflected light collected by the light guide to vary. In addition, the system includes a light transmitter coupled to the light guide and a light detector coupled to the light guide. The light detector detects reflected light collected by the light guide, facilitating sensing of the movements of the reflection element and the timing of the motion of tissue stably associated therewith, e.g., cardiac wall motion.

In certain embodiments, the reflective element is a mirror, such as a micro-machined mirror. The mirror can be attached (e.g., hinged) through one or more, e.g., a set of, torsion beams to a frame, where in certain embodiments the number of beams attaching the mirror to the frame is two. In certain embodiments, the center of mass of the mirror is located outside an axis of rotation corresponding to the torsion beams, whereby motion of a chip containing the mirror in a direction substantially orthogonal to the axis causes the mirror to move.

In certain embodiments, the reflective element includes a double-axis mirror. The double-axis mirror is hinged through a first set (e.g., two) of torsion beams to a first frame. The first frame is hinged to a second frame through a second set of (e.g., two) torsion beams. The center of mass of the mirror is located outside both a first axis of rotation corresponding the first set of torsion beams and a second axis of rotation corresponding the second set of torsion beams such that motion of a chip containing the mirror in a direction substantially orthogonal to either the first axis or the second axis causes the mirror to move.

In certain embodiments, the sensor is referred to herein as a transducer (in view of its function in transforming mechanical tissue movement into an optical signal) and may be configured in the form of a chip which may have a variety of different configurations and includes a reflective element, such as a mirror, attachment members, such as torsional beams, a frame and any support structure, as developed in greater detail below.

In certain embodiments, the light guide is an optical fiber, such as a single-mode or a multi-mode optical fiber.

The system may also include a collimating element (i.e., a collimating mechanism) located at the distal end of the optical fiber, e.g., integrated with or separate from the distal end of the optical fiber, such that the collimating element is optically coupled to the distal end of the optical fiber. In such embodiments, light emitting from the optical fiber may be better directed toward the reflection mechanism. In addition, sensitivity of the sensing of movements of the reflection mechanism may be increased.

The collimating element may be constructed using a collimating lens, which can be selected from a convex lens, a plano-convex lens, or a graded index (GRIN) lens among others. Another way to obtain collimated light is to use a lensed optical fiber. Alternatively, a fiber with an expanded core can be used, so that light emitting from the optical fiber is better collimated.

In one embodiment of the present invention, one end of the optical fiber is directed to the front of the chip which contains a micro-machined mirror. Correspondingly, the reflective surface of the mirror is the front side of the mirror. In another embodiment, one end of the optical fiber is situated within a cavity etched on the back of the chip which contains the micro-machined mirror. In this case, the reflective surface of the mirror is the back side of the mirror.

In another embodiment, the mirror resides within a hermetically sealed enclosure. This configuration provides the opportunity for the enclosure to be made sufficiently small so that the enclosure can be inserted into a lumen within a cardiac pacing lead. In one embodiment, the outer diameter of the enclosure is about 0.025 to about 0.6 mm, such as about 0.1 to about 0.5 mm, including from about 0.25 to about 0.40 mm. The enclosure can be made of an inert material, which may include stainless steel, platinum, nickel, cobalt, chromium, or an alloy thereof, among others.

In one embodiment of the present invention, the optical fiber is situated within a metal coil. The outer diameter of the metal coil is sufficiently small so that the metal coil may be inserted into the lumen within a vascular, e.g., cardiac pacing, lead. In one embodiment, the outer diameter of the metal coil is about 0.025 to about 0.6 mm, such as from about 0.1 to 0.5 mm, including from about 0.25 to about 0.40 mm. The metal coil can be made of an inert material, which may include stainless steel, platinum, nickel, cobalt, chromium, or an alloy thereof, among others.

In another embodiment of the present invention, the system includes a main optical fiber for carrying a number of wavelengths and a number of branch fibers, where each branch fiber includes a transducer having a movable reflective element, e.g., mirror, located at its distal end. Each branch fiber may be coupled, as desired, to the main fiber through a wavelength-selective mechanism. The system may also include, as desired, a wavelength-division multiplexer/demultiplexer coupled to the main fiber. This multiplexer/demultiplexer can multiplex a number of wavelengths into the main fiber, thereby allowing each timer to operate at a different wavelength. In addition, this multiplexer/demultiplexer demultiplexes the light reflected by the timers into different wavelengths, facilitating individual detection of the light reflected by each timer.

In another embodiment of the present invention, a guide wire is inserted through a blood vessel of a patient into the patient's heart. A cardiac pacing lead is then slid onto the guide wire. Next, the guide wire is retrieved from the pacing lead. A fiberoptic cardiac wall motion timer is subsequently inserted through a lumen within the pacing lead, thereby allowing the fiberoptic cardiac wall motion timer to detect movements of the heart.

In another embodiment, the fiberoptic cardiac wall motion timer comprises a micro-machined movable mirror and an optical fiber. The optical fiber is situated within a metal coil whose outer diameter is sufficiently small so that the metal coil can be inserted into the lumen within the cardiac pacing lead. Furthermore, inserting the fiberoptic cardiac wall motion timer through the lumen within the pacing lead involves inserting the metal coil through the lumen.

In one embodiment of the present invention, a guide wire is inserted through a blood vessel of a patient into the patient's heart, wherein the guide wire includes a metal coil, a fiberoptic cardiac wall motion timer, and an optical fiber at a minimum. The system then transmits light into the optical fiber, allowing the fiberoptic cardiac wall motion timer to detect movement of the patient's heart. The system also detects light reflected from the fiberoptic cardiac wall motion timer.

DETAILED DESCRIPTION

Figure 1:
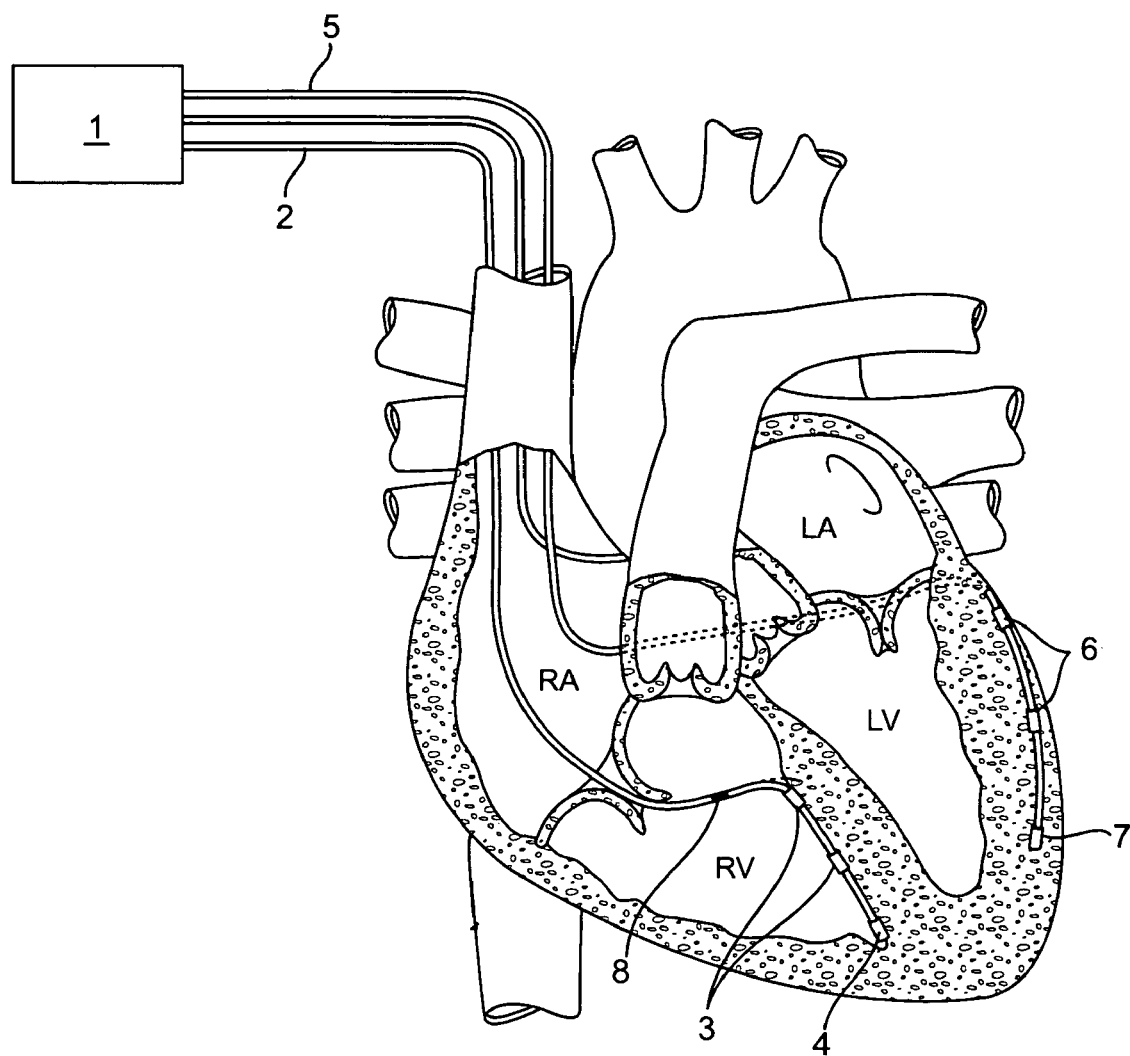
FIG. 1 illustrates the location of a number of fiberoptic cardiac wall motion timers in accordance with an embodiment of the present invention.

Devices and methods for evaluating motion of a tissue location, such as cardiac tissue location, e.g., heart wall, are provided. Devices employed in the subject methods are fiberoptic tissue motion sensors that include a light guide having a reflective element at its distal end and a light emitter and detector at its proximal end. In embodiments of the methods, a signal obtained from reflective element stably associated with the tissue location of interest is employed to evaluate movement of the tissue location. The subject methods and devices find use in a variety of different applications, including cardiac resynchronization therapy.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing the subject invention, a general review of the subject methods and systems as well as various aspects thereof is first provided. Next, a more detailed review of specific embodiments with reference to various figures is provided. Following this section, representative applications in which the subject invention finds use are described, as well as other aspects of the invention, such as computer related embodiments and kits that find use in practicing the invention.

Overview of Tissue Motion Characterization Using Fiberoptic Motion Sensors

As summarized above, the subject invention provides methods for evaluating movement of a tissue location, e.g., a cardiac tissue location, of interest by using a fiberoptic tissue motion sensor. In the subject methods, data obtained by a fiberoptic tissue motion sensor stably associated with the tissue location of interest is employed. In certain embodiments, the data which is employed at least includes, and sometimes solely includes, the timing of a signal obtained from one or more fiberoptic tissue motion sensors of the invention. An embodiment of the present fiberoptic tissue motion sensor is configured to provide information on wall motion for cardiac resynchronization therapy, such as for the treatment of congestive heart failure. Aspects of the invention provide fiberoptic tissue motion sensors positioned in or on the heart for determining cardiac wall contraction synchrony and/or dissynchrony.

Embodiments of the invention include the use of fiberoptic tissue sensors to obtain information based on timing and deflection of the sensors. In these embodiments, the measurement is a simple signal, measuring whether or not tissue movement is occurring; and therefore indicating whether or not the muscle is contracting. By way of example, when a fiberoptic tissue motion sensor is placed in a cardiac vein that runs along the endocardial aspect of wall of the left ventricle, data is provided to the clinician as to the timing of left ventricular wall movement. These data can be obtained using one or more tissue motion sensors, depending on the specific application. In contrast to currently employed methods using pressures and/or Tissue Doppler Imaging (TDI), the use of the present invention allows the clinician to directly measure from just this sort of on/off motion sensor, whether or not the two particular cardiac chambers are contracting at the same time. More important is the determination of whether the septal and free wall contractive elements of the left ventricle are also contracting at the most optimal time for continuing to cardiac output. These particular applications are reviewed below in greater detail.

Aspects of the fiberoptic tissue motion sensors employed in embodiments of the invention are the presence of one or more transducers that generate a signal, e.g., optical etc., in response to an applied stimulus, e.g., deflection, bending, stretching, etc. In embodiments of the invention, the transducer includes a light guide having a reflective element at its distal end, as reviewed in great detail below. Movement of the reflective element in response to movement of tissue with which the reflective element is stably associated modulates light traveling from the reflective element to the proximal end of the light guide, and thereby transduces the tissue motion into a light signal. In certain embodiments, the transducer is incorporated into a medical device at or under surface of the device. The transducer provides a signal when the tissue location of interest moves, since the transducer is stably associated with the tissue location of interest.

In certain embodiments, the sensors are implantable pressure sensors. In these embodiments, the implantable pressure sensors are sensors that may be positioned in or on a body and function without significant, if any, deterioration for extended periods of time. As such, once implanted, the subject sensors do not deteriorate in terms of function for a period of at least about 2 or more days, such as at least about 1 week, at least about 4 weeks, at least about 6 months, at least about 1 year or longer, e.g., at least about 5 years or longer.

As summarized above, the subject invention provides methods of evaluating movement of a tissue location. "Evaluating" is used herein to refer to any type of detecting, assessing or analyzing, and may be qualitative or quantitative. In certain embodiments, movement is determined relative to another tissue location, such that the methods are employed to determine movement of two or more tissue locations relative to each other.

The tissue location(s) is generally a defined location or portion of a body, i.e., subject, where in representative embodiments it is a defined location or portion (i.e., domain or region) of a body structure, such as an organ, where in representative embodiments the body structure is an internal body structure, such as an internal organ, e.g., heart, kidney, stomach, lung, etc. In certain embodiments, the tissue location is a cardiac location. As such and for ease of further description, the various aspects of the invention are now reviewed in terms of evaluating motion of a cardiac location.

The cardiac location may be either endocardial or epicardial, as desired, and may be an atrial or ventricular location. Where the tissue location is a cardiac location, in certain embodiments, the cardiac location is a heart wall location, e.g., a chamber wall, such as a ventricular wall, a septal wall, etc. Although the invention is now further described in terms of cardiac motion evaluation embodiments, the invention is not so limited, the invention being readily adaptable to evaluation of movement of a wide variety of different tissue locations.

In practicing embodiments of the invention, following implantation of any required elements in a subject (e.g., using known surgical techniques), the signal (representing data) from a fiber optic tissue motion sensor that is stably associated with the tissue location of interest is then detected to evaluate movement of the tissue location. As reviewed above, in certain embodiments the timing of the signal obtained from the sensing element is employed, e.g., in characterizing movement of the tissue location of interest.

By "stably associated with" is meant that the transducer is substantially if not completely fixed relative to the tissue location of interest such that when the tissue location of interest moves, the transducer also moves. As the employed transducer is stably associated with the tissue location, its movement is the same as (or at least a proxy for such that it serves as a suitable indicator of) the movement of the tissue location to which it is stably associated. The transducer may be stably associated with the tissue location using any convenient approach, such as by attaching the transducer to the tissue location by using an attachment element, such as a hook, etc., by having the transducer on a structure that compresses the transducer against the tissue location such that the two are stably associated, etc.

In a given embodiment, the transducer can provide output in an interval fashion or continuous fashion for a given duration of time, as desired.

In certain embodiments, a single transducer is employed. In such methods, evaluation may include monitoring movement of the tissue location over a given period of time. In certain embodiments, two or more distinct transducers are employed to evaluate movement of two or more distinct tissue locations. The number of different transducers that are employed in a given embodiment may vary greatly, where in certain embodiments the number employed is 2 or more, such as 3 or more, 4 or more, 5 or more, 8 or more, 10 or more, etc. In such multi-transducer embodiments, the methods may include evaluating movement of the two or more distinct locations relative to each other.

In certain embodiments, the subject methods include providing a system that includes a fiberoptic tissue motion sensor having a transducer that is stably associated with the tissue location of interest. This providing step may include implanting one or more new elements into a body. This step, if employed, may be carried out using any convenient protocol.

The subject methods may be used in a variety of different kinds of animals, where the animals are in certain embodiments "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g., rabbits) and primates (e.g., humans, chimpanzees, and monkeys). In certain embodiments, the subjects or patients will be humans.

The tissue movement evaluation data obtained using the subject methods may be employed in a variety of different applications, including but not limited to monitoring applications, treatment applications, etc. Representative applications in which the data obtained from the subject methods finds use are further reviewed in greater detail below.

General Design Considerations

The following section reviews a number of different features of different aspects of certain embodiments of the invention.

Post Processing Steps

The analysis of the data obtained from a transducer(s) in accordance with embodiments of the invention may benefit from post processing to determine the timing of the motion. In certain embodiments of the device, signal processing is performed. For example, a signal from the device drives an auditory device that relays timing signals to the clinician as a series of tones. The clinician, prompted by these tones, then measures and adjusts the timing of the cardiac muscle by listening to different frequency tones that converged to one frequency as the timing of the heart was improved. A visual signal can also be derived from the timing information. A series of lights is produced from the signal that would change from red to green as the change in timing of the cardiac muscle was improved.

Fabrication

The transducers selected or developed for the inventive tissue motion sensors may be constructed using any convenient fabrication method. Any of a variety of different protocols may be employed in manufacturing the structures and components thereof of the invention. For example, molding, deposition and material removal, e.g., planar processing techniques, such as Micro-Electro-Mechanical Systems (MEMS) fabrication, may be employed. Deposition techniques that may be employed in certain aspects of fabrication the structures include, but are not limited to: electroplating, cathodic arc deposition, plasma spray, sputtering, e-beam evaporation, physical vapor deposition, chemical vapor deposition, plasma enhanced chemical vapor deposition, etc. Material removal techniques included, but are not limited to: reactive ion etching (RIE), anisotropic chemical etching, isotropic chemical etching, planarization, e.g., via chemical mechanical polishing, laser ablation, electronic discharge machining (EDM), etc. Also of interest are lithographic protocols. Of interest in certain embodiments is the use of planar processing protocols, in which structures are built up and/or removed from a surface or surfaces of an initially planar substrate using a variety of different material removal and deposition protocols applied to the substrate in a sequential manner.

Positioning of Transducers in Device, and Device in Body

The location of the transducer in the body of the cardiac timing device directly impacts the significance of signal which it transmits. During insertion of the cardiac timing device, it is possible to fine tune the location of the transducer (s). The optimal positioning of transducers within the device is also pivotal in providing the best possible cardiac timing information from the device.

Positioning of the transducers both within the device and within the body provides for optimum motion signal and motion timing for detection of heart wall motion. In certain embodiments, the positioning of the transducer within the device or positioning means will be off the neutral axis. The positioning can also be provided at the outside edge around the diameter of the device. Optimal location of the transducer components within the cardiac timing device are determined as a function of the bending stiffness of the material of which the lead or other device body components, such as the catheter device are composed.

If the material of the cardiac timing device body components is selected from within a relatively soft range, there is the opportunity for the transducer component to be implanted more deeply into the device without disadvantageously compromising sensing capabilities. Examples of such materials are silicone and its derivatives. Conversely, if the material of the cardiac timing device body is more rigid, the transducer component will typically be implanted less deep into the device. A typical example of such harder materials is polyurethane.

Where multiple transducers are used, it is advantageous to separate them from the mechanical strain from adjacent sections of the body of the device. This can be accomplished by providing softer material in areas of the body of the device between locations where the transducer components are embedded. This approach serves to mechanically isolate the transducer components from each other. This approach can ameliorate or obviate a potential risk of strain from one section of the device being transmitted through the device to another section.

Methods Overview

A simple application of the inventive tissue motion sensor is to place catheters, with tissue motion sensors attached, on both the left ventricular free wall, the right ventricular free wall, and potentially directly on the septum. This placement of the inventive device produces a very simple signal indicating when each of these cardiac features is contracting, the amplitude and time course of the contraction, and in some configurations their direction of movement.

When combined with pressure readings from other sensors, the present invention allows the comparison of contraction timing and the pressure changes in the ventricles. A prior art data point for CRT therapy has been pressure-pressure loops. In the general case it is thought that in the healthy heart, both ventricles contract at the same time. In that case, peak pressure would be achieved in both ventricles simultaneously. This test has been employed as a measure of potential synchrony. In dissynchronous hearts, the pressure peak typically occurs at different times, suggesting that the muscle is contracting at different times. This difference in contraction can be directly measured with the present inventive motion sensors. Comparison to RV and/or LV pressures will add additional global data over fiber optic tissue motion sensors alone.

In an additional embodiment of the present invention, the transducer is attached to the ventricular septum, the wall between the two ventricles. Cardiologists often characterize the septum moving much like a sail. If pressure peaks are occurring at different times in the ventricles, the septum bows into whichever ventricle is at the lowest pressure. If the left ventricle compresses later than the right ventricle, the right ventricle will be in a relaxation phase during the LV contraction. In this case, the septum is likely to deflect into the right ventricle. By measuring the direction and/or timing of the deflection of the septum related to pressure changes, the clinician can determine, without even measuring a left ventricular pressure, when the pressure peak is occurring in the left ventricle.

An additional use of the present tissue motion sensors is to determine apex movement. In this case, a motion sensor is placed near or at the tip of a device at the apex of one of the ventricles, left or right. These devices provide a measure of when the apex is moving. A number of parameters can be measured by this device placement. By example, the timing of apical contraction can be determined, as well as changes in the amplitude of the contraction. This sensing capacity can be provided by one of the following features.

In general, two types of data are collected in certain embodiments of the invention. In the simplest case, the timing of the motion is collected by simply analyzing when the contractions occur. This case could also be used as a method to measure the difference between contractions that occur before, during and after CRT optimization. The actual amplitude of the contractions is not important, only the difference between the contractions before and after an optimization procedure.

An additional application of the inventive system is to place catheters, with transducers attached, on the left ventricular free wall, the right ventricular free wall, and potentially directly on the septum. Such a configuration produces direct, motion-derived signals indicating when each of these cardiac features is contracting, and the respective amplitude and time course of the contractions.

Additional Features Found in Representative Systems

Embodiments of the subjects systems incorporate other physiologic sensors in order to improve the clinical utility of wall-motion data provided by the present invention. For example, an integrated pressure sensor provides, in certain embodiments, a self-optimizing cardiac resynchronization pacing system with an important verification means, since wall motion optimization in the face of declining systemic pressure would be an indication of improper pacing, component failure or other underlying physiologically deleterious condition (e.g., hemorrhagic shock). One or more pressure sensors also provides, in certain embodiments, important information used in the diagnosis of malignant arrhythmias requiring electrical intervention (e.g., ventricular fibrillation)

Incorporation of other sensors is also envisioned. Some of the present inventors have developed Doppler, pressure sensors, additional wall motion, and other cardiac parameter sensing devices, which devices or at least components thereof can be present in medical devices according to embodiments of the invention, as desired. Some of these are embodied in currently filed provisional applications; "One Wire Medical Monitoring and Treating Devices", U.S. Provisional Patent Application No. 60/607,280 filed Sep. 2, 2004, U.S. patent application Ser. No. 11/025,876 titled "Pressure Sensors having Stable Gauge Transducers"; U.S. patent application Ser. No. 11/025,366 "Pressure Sensor Circuits"; U.S. patent application Ser. No. 11/025,879 titled "Pressure Sensors Having Transducers Positioned to Provide for Low Drift"; U.S. patent application Ser. No. 11/025,795 titled "Pressure Sensors Having Neutral Plane Positioned Transducers"; U.S. patent application Ser. No. 11/025,657 titled "Implantable Pressure Sensors"; U.S. patent application Ser. No. 11/025,793 titled "Pressure Sensors Having Spacer Mounted Transducers"; "Stable Micromachined Sensors" U.S. Provisional Patent Application 60/615,117 filed Sep. 30, 2004, "Amplified Complaint Force Pressure Sensors" U.S. Provisional Patent Application No. 60/616,706 filed Oct. 6, 2004, "Cardiac Motion Characterization by Strain Measurement" U.S. Provisional Patent Application filed Dec. 20, 2004, and PCT Patent Application entitled "Implantable Pressure Sensors" filed Dec. 10, 2004, "Shaped Computer Chips with Electrodes for Medical Devices" U.S. Provisional Patent Application filed Feb. 22, 2005; "Fiberoptic Cardiac Wall Motion Timer" U.S. Provisional Patent Application 60/658,445 filed Mar. 3, 2005; "Cardiac Motion Detection Using Fiberoptic Strain Gauges" U.S. Provisional Patent Application 60/667, 749 filed Mar. 31, 2005. These applications are incorporated in their entirety by reference herein.

Systems in which the present fiberoptic motions sensors may be incorporated vary widely. Devices and systems in which the subject sensors find use include, but are not limited to, those described in: WO 2004/066817 titled "Methods And Systems For Measuring Cardiac Parameters"; WO 2004/066814 titled "Method And System For Remote Hemodynamic Monitoring"; WO 2005/058133 titled "Implantable Pressure Sensors"; WO 2004/0521-82 titled "Monitoring And Treating Hemodynamic Parameters"; WO 2004/067081 titled "Methods And Apparatus. For Enhancing Cardiac Pacing"; U.S. Provisional Patent Application 60/638,928 entitled "Methods and Systems for Programming and Controlling a Cardiac Pacing Device" filed Dec. 23, 2004; U.S. Provisional Patent Application No. 60/658,445 titled "Fiberoptic Cardiac Wall Motion Timer" filed Mar. 3, 2005; U.S. Provisional Patent Application No. 60/667,759 titled "Cardiac Motion Detection Using Fiberoptic Strain Gauges," filed Mar. 31, 2005; U.S. Provisional Patent Application No. 60/679,625 titled "de Minimus Control Circuit for Cardiac pacing and Signal Collection," filed May 9, 2005; U.S. Provisional Patent Application No. 60/706,641 titled "Deployable Epicardial Electrode and Sensor Array," filed Aug. 8, 2005; U.S. Provisional Patent Application No. 60/705,900 titled "Electrical Tomography" filed Aug. 5, 2005; U.S. Provisional Patent Application No. 60/707,995 titled "Methods and Apparatus for Tissue Activation and Monitoring" filed Aug. 12, 2005; U.S. Provisional Patent Application No. 60/707,913 titled "Measuring Conduction Velocity Using One or More Satellite Devices," filed Aug. 12, 2005. These applications are herein incorporated into the present application by reference in their entirety.

In the implantable embodiments of this invention, wall motion, pressure and other physiologic data can be recorded by an implantable computer as desired. Such data can be periodically uploaded to computer systems and computer networks, including the Internet, for automated or manual analysis.

Uplink and downlink telemetry capabilities may be provided in a given implantable system to enable communication with either a remotely located external medical device or a more proximal medical device on the patient's body or another multi-chamber monitor/therapy delivery system in the patient's body. The stored physiologic data of the types described above as well as real-time generated physiologic data and non-physiologic data can be transmitted by uplink RF telemetry from the system to the external programmer or other remote medical device in response to a downlink telemetry transmitted interrogation command. The real-time physiologic data typically includes real time sampled signal levels, e.g., intracardiac electrocardiogram amplitude values, and sensor output signals including dimension signals developed in accordance with the invention. The non-physiologic patient data includes currently programmed device operating modes and parameter values, battery condition, device ID, patient ID, implantation dates, device programming history, real time event markers, and the like. In the context of implantable pacemakers and ICDs, such patient data includes programmed sense amplifier sensitivity, pacing or cardioversion pulse amplitude, energy, and pulse width, pacing or cardioversion lead impedance, and accumulated statistics related to device performance, e.g., data related to detected arrhythmia episodes and applied therapies. The multi-chamber monitor/therapy delivery system thus develops a variety of such real-time or stored, physiologic or non-physiologic, data, and such developed data is collectively referred to herein as "patient data".

Specific Embodiments and Systems

In further describing aspects of the subject invention, various representative systems and methods for their use are reviewed in terms of figures.

Location of Fiberoptic Cardiac Wall Motion Timers

FIG. 1 illustrates the location of a number of fiberoptic cardiac wall motion timers in accordance with an embodiment of the present invention. As shown in this example, communication means 1 provides the extracardiac communication and calculation means for the overall system. Communication means 1 can take the form of various embodiments including an implantable device complete with power supply, drive electronics and processing power on board. In more complex configurations, communication means 1 may provide a means for communicating data and power from a completely external or extracorporeal location.

Right ventricular lead 2 emerges from communication device in communication means 1, and travels from a subcutaneous location of communication means 1 via the subclavian venous access through the superior vena cava through the right atrium and then through the tricuspid valve to a position along the right ventricle. In the illustrated embodiment, this location is located along its distal portion in close association with the intraventricular septum terminating distally with fixation in the right ventricular apex.

Particular to distal aspect of right ventricular lead 2 are fiberoptic cardiac wall motion timers 3 and 4. In other embodiments of the present invention, an additional number or smaller number of sensors may be employed.

Additionally emerging at the proximal aspect of communication means 1 is left ventricular lead 5. Left ventricular lead 5 starts by following the same route as right ventricular lead 2 via subclavian vein through the superior vena cava into the right atrium. At this point, left ventricular lead 5 is placed via the coronary sinus around the posterior aspect of the heart and thence into cardiac vein draining into said sinus.

FIG. 1 further depicts left ventricular lead 5 in a position likely to be advantageous for biventricular pacing located along the lateral aspect of the left ventricle. Fiberoptic cardiac wall motion timers 6 and 7 in the left ventricular are analogous to timers 3 and 4 which are previously described.

Right ventricular lead 2 may optionally be provided with pressure sensor 8 which is located in the right ventricle. Pressure sensor 8 provides a pressure signal which can also simultaneously be obtained with wall motion data. In certain embodiments, adding active devices to the lead such as pressure sensor 8 is facilitated through the use of a multiplexing system, such as described in Published PCT Application No. WO 2004/052182 and U.S. patent application Ser. No. 10/734,490, the disclosure of which is herein incorporated by reference.

Principle of operation of fiberoptic cardiac wall motion timers 3, 4, 6, and 7 is that communication means 1 communicates with each of the sensors. Cardiac movement signals detected by each timer are then obtained, e.g., in the form of timing of the signals.

Figure 2:
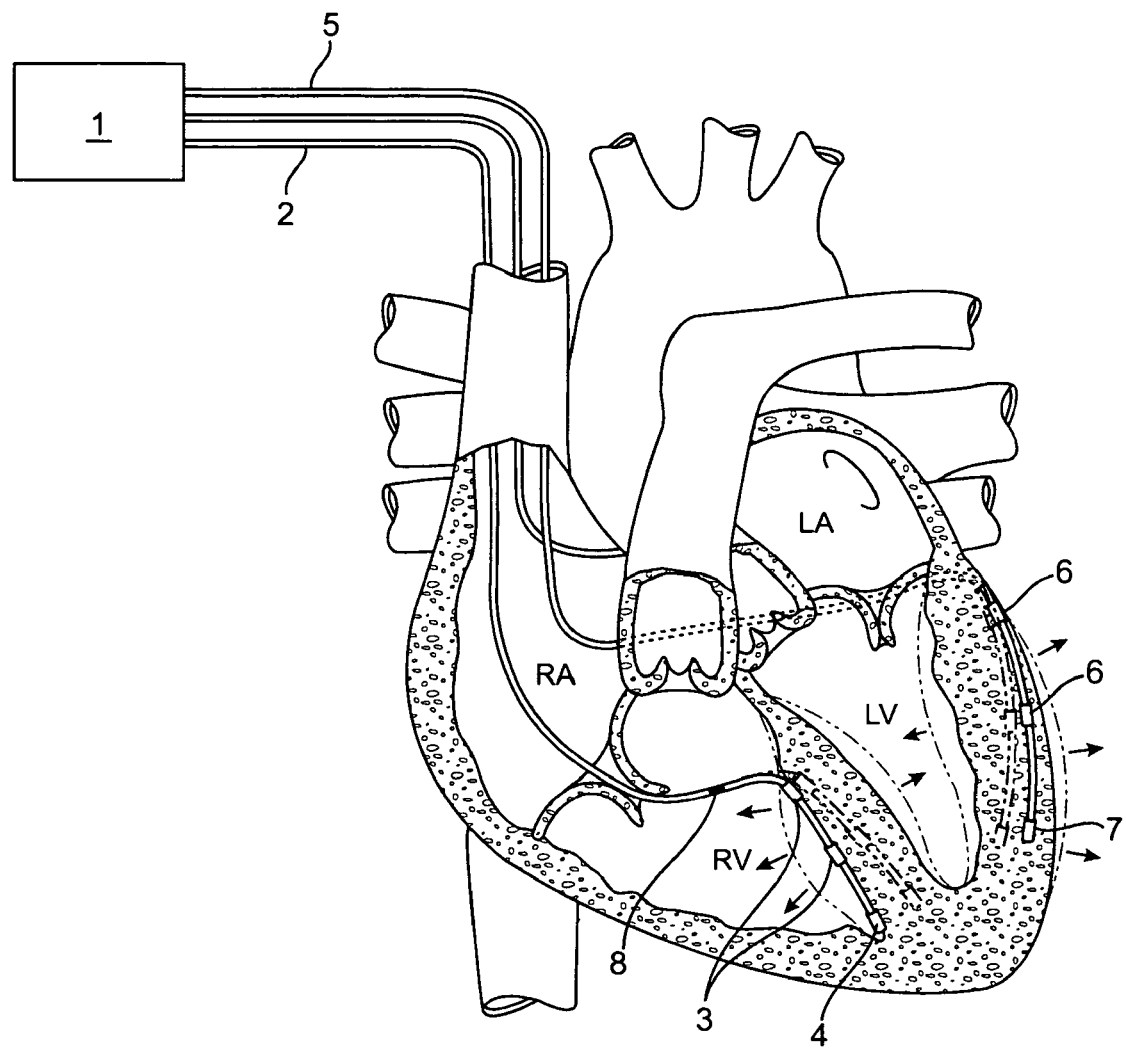
FIG. 2 illustrates the location of a number of fiberoptic cardiac wall motion timers showing additionally the cardiac motion in accordance with an embodiment of the present invention.

FIG. 2 illustrates the location of a number of fiberoptic cardiac wall motion timers showing additionally the cardiac motion in accordance with an embodiment of the present invention. As shown in FIG. 2, right ventricular lead 2 and left ventricular lead 5 are provided in close association with the wall of the heart. As the wall of the heart moves via 3D cardiac cycle, so do the leads in a proportionate amount. As these leads move towards and away from one another, the range and velocity information varies over the course of the cardiac cycle. This variation is indicative of their movement and the timing thereof.

The cardiac motion data together with an optional pressure signal or signals is used in a variety of different applications, such as to optimize cardiac resynchronization therapy where the goal is to maximize the contractility of the left ventricle. This is obtained by encouraging effectively simultaneous contraction of the bulk of the muscle of the left ventricle. In many congestive heart failure patients, such contractility is impaired with dyskinetic contraction, which typically occurs with a septal contraction against a relaxed left ventricle followed by ventricular contraction against a relaxing septum. The result is inefficiency with regards to the blood being moved around the ventricle rather than constrictively expelled from the ventricle as in a normal case.

Current systems provide biventricular pacing on an empiric basis only where optimization is attempted. It is generally a time-consuming process based on external cardiac ultrasound. A physician attempts to visualize wall motion. With the aid of tools in the ultrasound machine, the physician calculates a synchronicity index based on the wall motion just described. The current system would provide such data in real time and in a numeric format useable by both the implanting physician and by an automated pacing system such as a CRT device.

A fiberoptic cardiac wall motion timer of the present invention can detect abnormalities in wall motion associated with ischemia or arrhythmia and other cardiac abnormalities including progression of underlying disease states such as congestive heart failure. If connected to an external or fully implanted real time monitor, such abnormalities can trigger an alarm. This alarm alerts the patient or a physician of the advent of these abnormalities.

Operation of Fiberoptic Cardiac Wall Motion Timers

Figure 3:
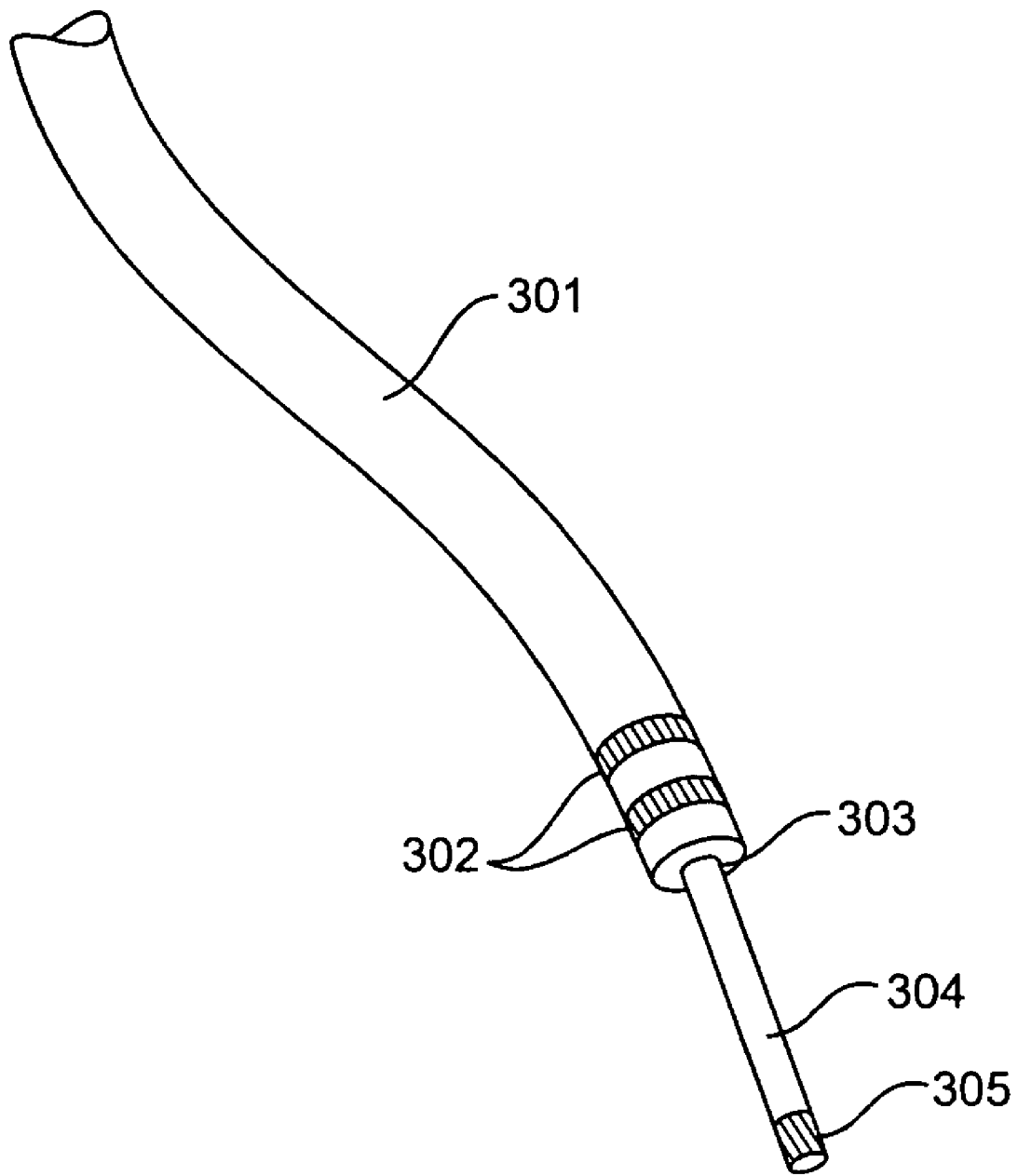
FIG. 3 illustrates a cardiac wall motion timer inserted through a pacing lead in accordance with an embodiment of the present invention.

FIG. 3 illustrates a cardiac wall motion timer inserted through a pacing lead in accordance with an embodiment of the present invention. Shown in this example is a cardiac pacing lead 301. A pacing lead typically has a number of electrodes, such as electrodes 302. Within pacing lead 302 is a lumen 303. In general, lumen 303 provides room for a physician to slide lead 301 onto a guide wire which is inserted-into a patient's blood vessel, such as guide wire 304.

In one embodiment of the present invention, a fiberoptic cardiac wall motion timer 305 is located at one end of guide wire 304. In certain embodiments, fiberoptic cardiac wall motion timer 305 is sufficiently small so that it can fit on guide wire 304 and can be inserted through lumen 303 of pacing lead 301. The small form factor of timer 305 allows a physician to implant or temporarily place timer 305 with a conventional CRT procedure.

Figure 4:
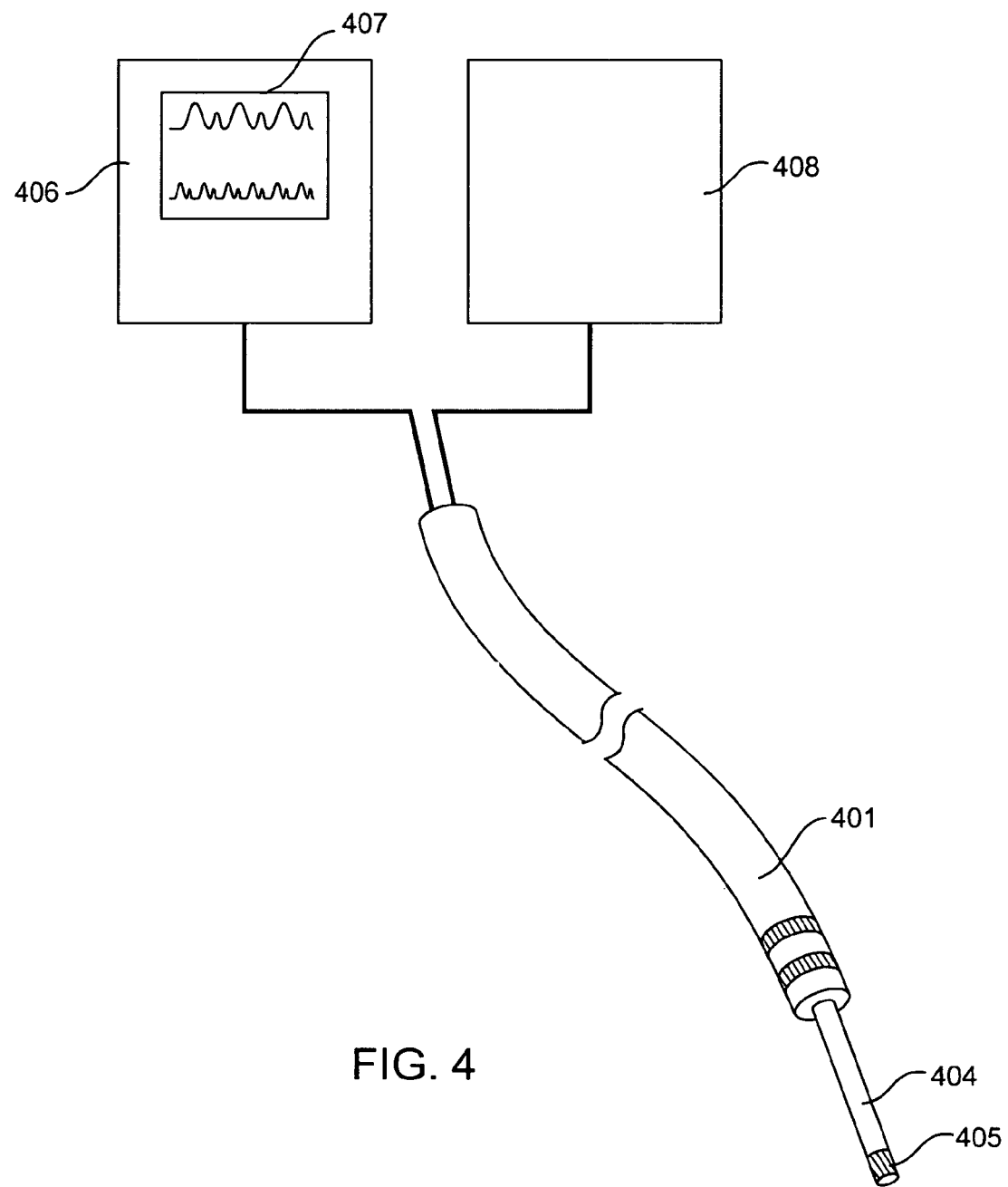
FIG. 4 illustrates the process of detecting cardiac motion with a cardiac wall motion timer inserted through a pacing lead in accordance with an embodiment of the present invention.

FIG. 4 illustrates the process of detecting cardiac motion with a cardiac wall motion timer inserted through a pacing lead in accordance with an embodiment of the present invention. In this example, a cardiac wall motion timer 405 is attached to a guide wire 404, which is inserted through the lumen of a pacing lead 401. Cardiac wall motion timer 405 is coupled to a monitoring unit 406. Monitoring unit 406 contains a display 407 which indicates cardiac parameters. In addition, display 407 may also present relevant information such as the electrocardiogram (EKG) or the pressure wave. The display of cardiac information can be performed simultaneously while a pacing controller 408 sends pacing pulses to the electrodes on pacing lead 401. In this way, a physician can monitor the cardiac parameters in real time while adjusting the timing of the pacing pulses.

Figure 5:
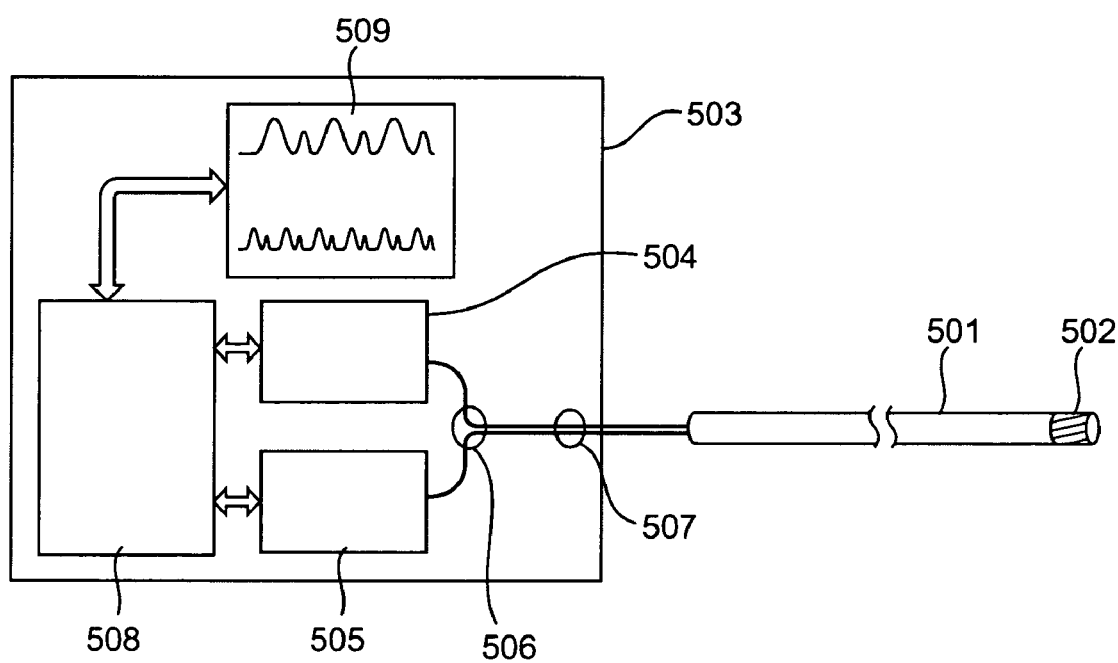
FIG. 5 illustrates the process of detecting cardiac motion with a fiberoptic cardiac wall motion timer inserted through a pacing lead in accordance with an embodiment of the present invention.

FIG. 5 illustrates the process of detecting cardiac motion with a fiberoptic cardiac wall motion timer inserted through a pacing lead in accordance with an embodiment of the present invention. A fiberoptic cardiac wall motion timer 502 which is attached to a guide wire 501 is coupled to a control unit 503. Control unit 503 contains a light source 504 and a light detector 505. Note that light source 504 can be a laser diode, a light emitting diode (LED), or other kind of light source. In addition, light detector 505 can be a photo diode or a photo multiplier tube.

Light source 504 and light detector 505 are coupled by a directional coupler 506 and a connector 507 to an optical fiber leading to fiberoptic cardiac wall motion timer 502. Directional coupler 506 allows light source 504 to send light to sensor 502 and allows light detector 505 to receive light reflected from sensor 502 with minimum interferences. In one embodiment of the present invention, directional coupler 506 is a 1×2 splitter.

As shown in FIG. 5, light source 504 and light detector 505 are also interfaced with a controller 508. Controller 508 is coupled to display 509 which presents the information contained in the cardiac wall motion timer signal.

Design of Fiberoptic Cardiac Wall Motion Timers

Figure 6A:
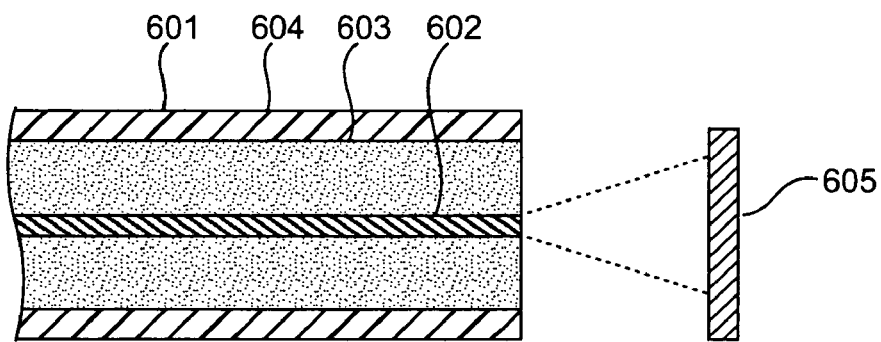
FIG. 6A illustrates a fiberoptic cardiac wall motion timer with its mirror in a normal position in accordance with an embodiment of the present invention.

FIG. 6A illustrates a fiberoptic cardiac wall motion timer with its mirror in a normal position in accordance with an embodiment of the present invention. In one embodiment of the present invention, a fiberoptic cardiac wall motion timer comprises an optical fiber 601 and a movable reflective mirror 605. Fiber 601 comprises a core 602, a cladding layer 603, and a protective buffer layer 604. Core 602 typically has a higher refractive index than cladding layer 603, so that core 602 and cladding layer 603 form a waveguide for light waves.

As shown in FIG. 6A, light emitting from fiber 601 is directed to mirror 605 and consequently is reflected off mirror 605. Mirror 605 is capable of tilting with the motion of the heart. As a result, the amount of reflected light that is collected by fiber 601 varies with the position of the mirror. Hence, by detecting the amount of reflected light, the system can sense the cardiac motion which causes mirror 605 to tilt.

Figure 6B:
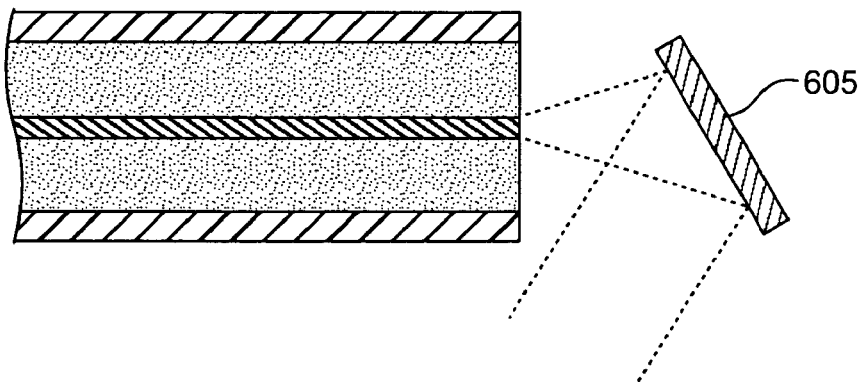
FIG. 6B illustrates a fiberoptic cardiac wall motion timer with its mirror in a tilted position in accordance with an embodiment of the present invention.

FIG. 6B illustrates a fiberoptic cardiac wall motion timer with its mirror in a tilted position in accordance with an embodiment of the present invention. In this example, mirror 605 is in a tilted position, which is caused by the motion of the heart where the sensor is situated. As shown in FIG. 6B, a substantial portion of the reflected light is not captured by the fiber.

Because the light exiting a regular cleaved optical fiber diverges quickly, in certain embodiments, the light is collimated in order to increase the sensitivity of the sensor. The loss of the reflected light without any collimation is:

$$L = 4.34 \times \left(\frac{2 \cdot \theta}{NA}\right)^2$$

where L is the optical loss in dB, $\theta$ is the rotation angle of the mirror and NA is the numerical aperture of the fiber. In contrast, the loss of the reflected light with collimation is:

$$L = 4.34 \times \left(\frac{2 \cdot \theta \cdot f}{\omega_0}\right)^2$$

where f is the focal length of a collimating lens and $\omega_0$ is the mode-field diameter of the light. For a typical single-mode fiber, the numerical aperture is on the order of about 5 degrees, whereas the mode-field diameter is on the order of about 5 μm. The focal length of a lensed fiber is on the order of about 2000 to 5000 μm. Consequently, collimation can improve the sensitivity of the sensor by about 100 times or more. Note that instead of a single-mode fiber, a multi-mode fiber can also be used. When a multi-mode fiber is used, the range of detection with respect to the mirror's rotation angle is increased.

Figure 7:
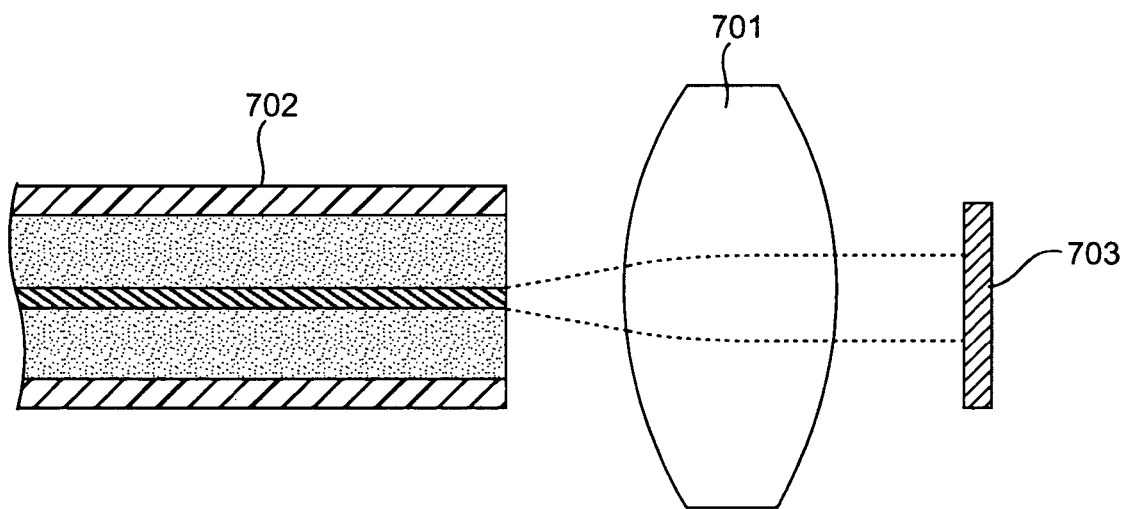
FIG. 7 illustrates a fiberoptic cardiac wall motion timer with a convex collimating lens in accordance with an embodiment of the present invention.

FIG. 7 illustrates a fiberoptic cardiac wall motion timer with a convex collimating lens in accordance with an embodiment of the present invention. As shown in this example, light emitting from fiber 702 is collimated by a convex lens 701 and is reflected by mirror 703. The reflected light is focused by lens 701 and captured by fiber 702. Note that although the example in FIG. 7 includes a convex lens, a plano-convex lens can also be used, among other types of collimating elements.

Figure 8:
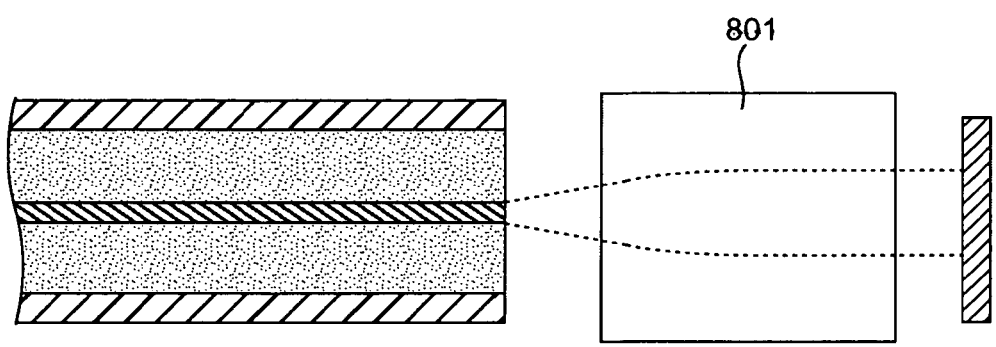
FIG. 8 illustrates a fiberoptic cardiac wall motion timer with a graded index (GRIN) collimating lens in accordance with an embodiment of the present invention.

FIG. 8 illustrates a fiberoptic cardiac wall motion timer with a graded index (GRIN) collimating lens in accordance with an embodiment of the present invention. In this example, a GRIN lens 801 is used to collimate the light emitting from the fiber.

Figure 9:
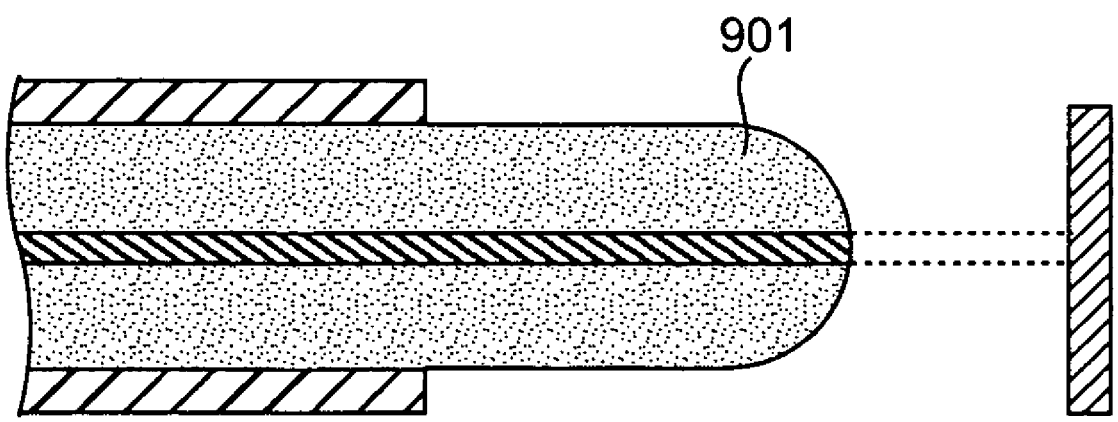
FIG. 9 illustrates a fiberoptic cardiac wall motion timer with a lensed fiber in accordance with an embodiment of the present invention.

Note that certain types of fibers have built-in or integrated collimation structure at one end, e.g., their distal end. If such fibers are used, there is no need to place a collimating lens between the fiber and the mirror. The advantage of using such fibers is that the form factor of the fiberoptic cardiac wall motion timer can be further reduced. FIG. 9 illustrates a fiberoptic cardiac wall motion timer with a lensed fiber in accordance with an embodiment of the present invention. As shown in FIG. 9, fiber 901 has a lensed end face, which collimates the exiting light.

Figure 10:
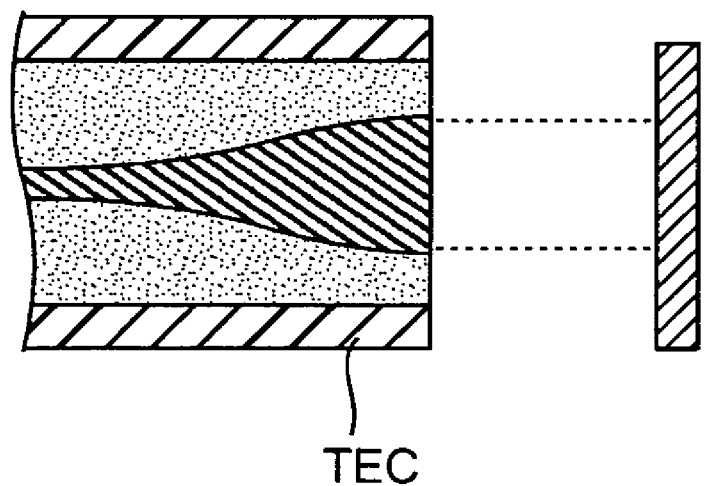
FIG. 10 illustrates a fiberoptic cardiac wall motion timer with a collimating fiber which has an expanded core in accordance with an embodiment of the present invention.

FIG. 10 illustrates a fiberoptic cardiac wall motion timer with a collimating fiber which has a thermally expanded core in accordance with an embodiment of the present invention. The expanded core allows more reflected light to be collected by the fiber. The embodiments depicted in FIGS. 9 and 10 illustrate devices with integrated collimating elements at their distal end.

Figure 11:
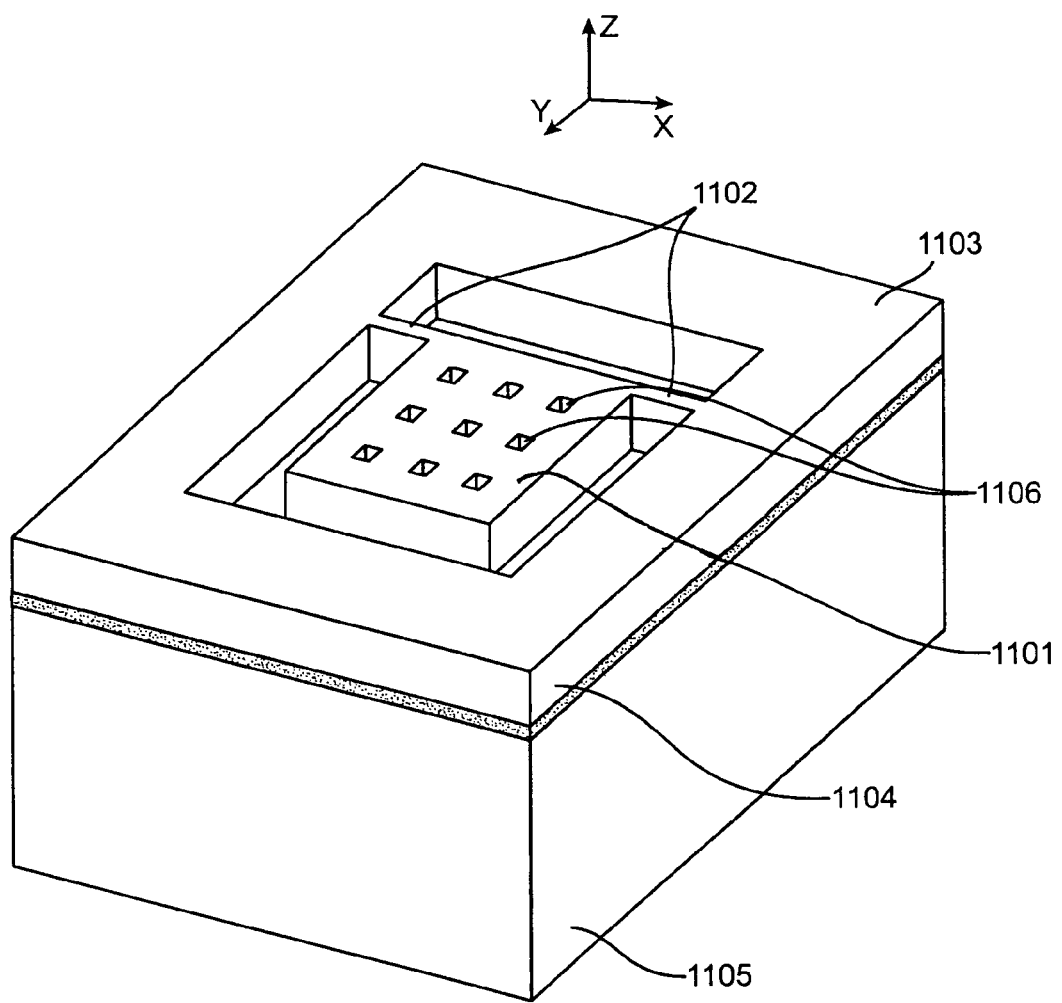
FIG. 11 illustrates a micro-machined single-axis mirror in accordance with an embodiment of the present invention.

FIG. 11 illustrates a micro-machined single-axis mirror in accordance with an embodiment of the present invention. In this perspective view, the depicted chip structure includes mirror element 1101 is hinged by two torsion beams 1102 to a frame 1103. Note that the center of mass of mirror 1101 is outside the axis along torsion beams 1102. This allows the inertia of mirror 1101 to cause mirror 1101 to tilt when the entire chip structure is moved, e.g., in response to movement of a tissue location with which the chip is stably associated. The mirror may be of varying dimension, e.g., from about to about 5000 μm, such as from about 20 to about 500 μm, and including from about 50 to about 200 μm. The thickness of the mirror may be about 0.1 μm to about 500 μm, such as from about 20 to about 100 μm, and including from about 5 to about 20 μm.

The structure illustrated in FIG. 11 can be fabricated with micro-machining techniques, where torsion beams 1102 and the anchor area are etched out of a device layer 1104 which is atop a silicon-on-insulator (SOI) wafer 1105. Also shown on mirror 1101 are etch holes 1106 which are used to facilitate the release of the mirror structure.

Note that the single-axis mirror structure shown in FIG. 11 is most sensitive to motion in the direction of z axis. It is also sensitive to motion in the direction of y axis. The structure is least sensitive to motion in the direction of x axis.

Figure 12:
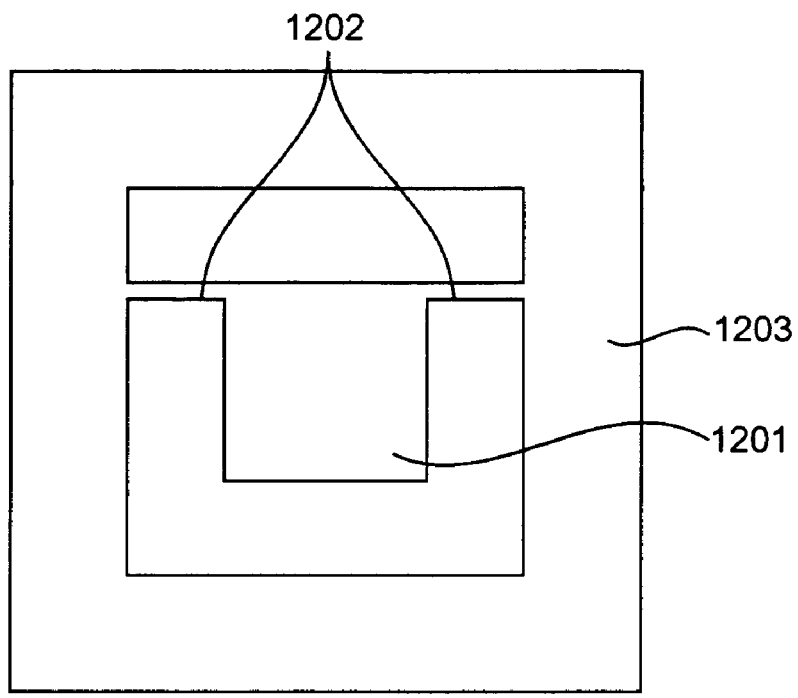
FIG. 12 illustrates the top view of a rectangular single-axis mirror in accordance with an embodiment of the present invention.

FIG. 12 illustrates the top view of a rectangular single-axis mirror in accordance with an embodiment of the present invention. Shown in FIG. 12 are mirror 1201, torsion beams 1202, and a frame area 1203.

Figure 13:
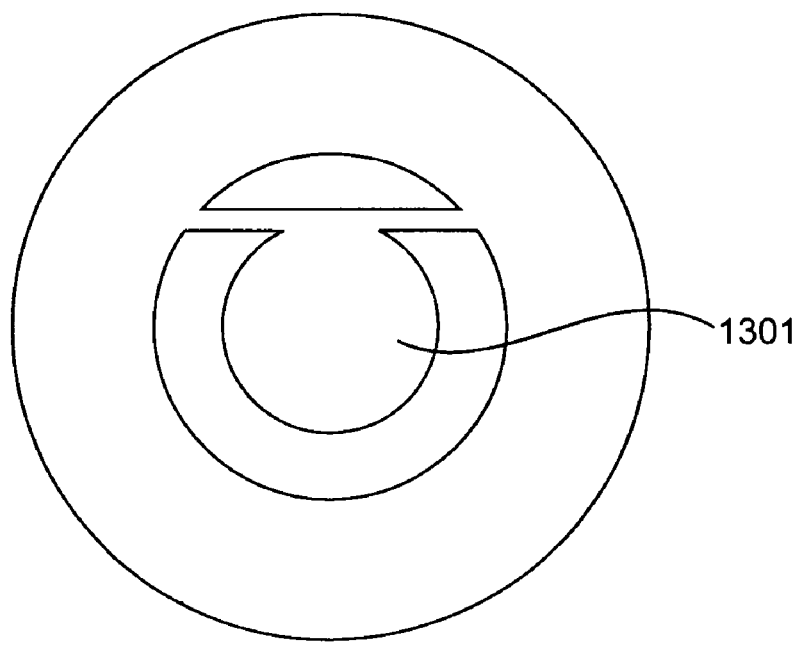
FIG. 13 illustrates the top view of a circular single-axis mirror in accordance with an embodiment of the present invention.

In some cases, one may desire a circular mirror which may fit better in a round-shaped enclosure. FIG. 13 illustrates the top view of a circular single-axis mirror in accordance with an embodiment of the present invention. In this example, both mirror 1301 and the frame area are circular. A round mirror can be particularly advantageous because the guide wire and catheter typically have a circular cross section.

While square and round mirror structures have been described and illustrated above, other shapes as desired may be employed.

A single-axis mirror, as shown in FIGS. 11-13, allows the mirror to tilt with motions substantially orthogonal to the axis along its torsion beams. However, if the motion is parallel to that axis, the mirror would be much less sensitive to such motion. To improve the sensitivity of the motion detection, one may construct a mirror with a gimbaled structure so that it can be sensitive to motion in any direction.

Figure 14:
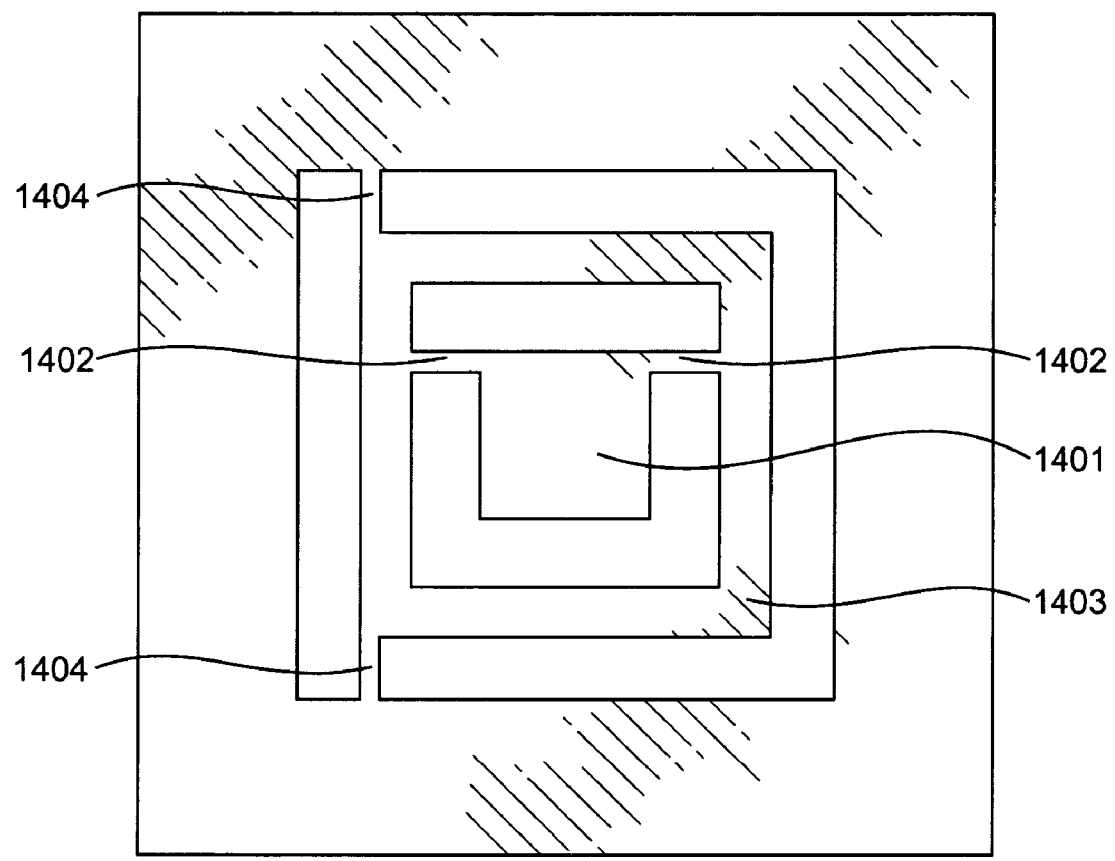
FIG. 14 illustrates the top view of a double-axis mirror with a gimbaled structure in accordance with an embodiment of the present invention.

FIG. 14 illustrates the top view of a double-axis mirror with a gimbaled structure in accordance with an embodiment of the present invention. In this example, a mirror 1401 is hinged to a first frame 1403 with torsion beams 1402. Frame 1403 is also hinged to the rest of the chip with its own torsion beams 1404. In this way, mirror 1401 can rotate around two axes and can be sensitive to motion in any of the x, y, and z directions.

Micro-Machining of the Mirror

Figure 15A:
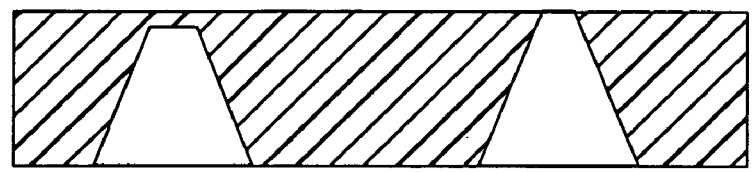
FIG. 15A illustrates the cross-section view of a single-axis mirror fabricated with bulk micro-machining in accordance with an embodiment of the present invention.
Figure 15B:
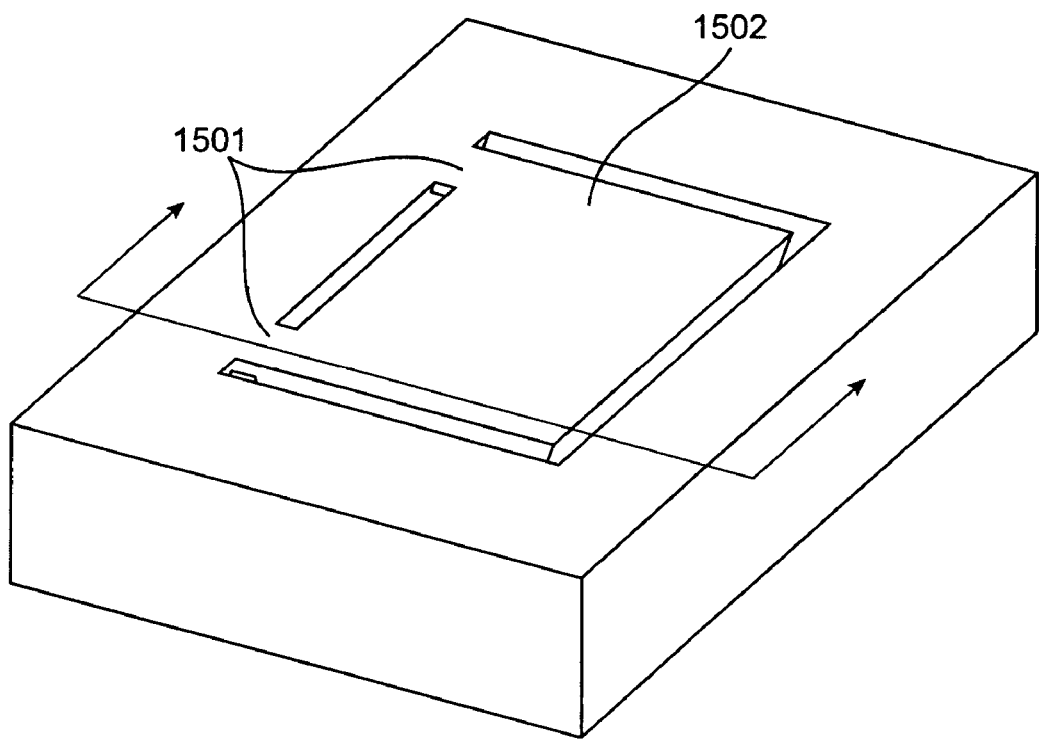
FIG. 15B illustrates the perspective view of a single-axis mirror fabricated with bulk micro-machining in accordance with an embodiment of the present invention.

The aforementioned mirror structures can be fabricated with either bulk micro-machining techniques or surface micro-machining techniques. FIG. 15A illustrates the cross-section view of a single-axis mirror fabricated with bulk micro-machining in accordance with an embodiment of the present invention. FIG. 15B illustrates the perspective view of a single-axis mirror fabricated with bulk micro-machining in accordance with an embodiment of the present invention.

As shown in FIG. 15B, the proof mass is wet etched to form torsion beams (i.e., springs) 1501 and to release mirror 1502. The reflective surface of mirror 1502 may be coated with a layer of material with high reflectivity, such as aluminum, gold, chromium, or silver, among others. Alternatively, one can use the dielectric surface of the mirror as the reflective surface. In one embodiment of the present invention, the mirror structure can be fabricated with tetramethylammonium hydroxide (TMAH) etching or potassium hydroxide (KOH) etching. The coating of the reflective surface can be done with physical vapor deposition or chemical vapor deposition.

Figure 16:
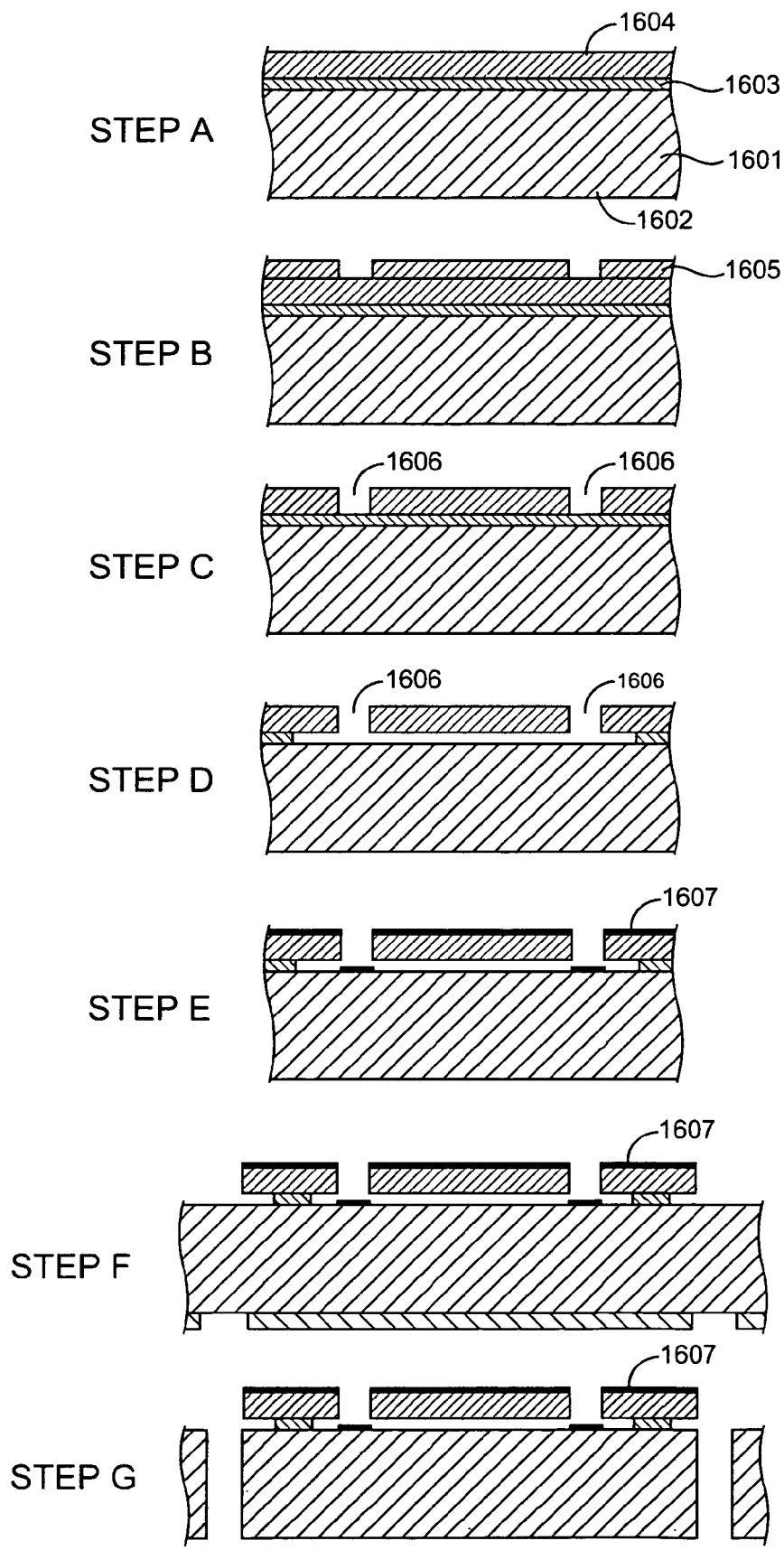
FIG. 16 illustrates an exemplary reactive ion etching (RIE) process for fabricating a mirror in accordance with an embodiment of the present invention.

FIG. 16 illustrates an exemplary reactive ion etching (RIE) process for fabricating a mirror in accordance with an embodiment of the present invention. As shown in initial step A, a wafer 1601 used in this example comprises a silicon handle layer 1602, a silicon dioxide ($SiO_2$) layer 1603, and a device layer 1604 which is typically made of single-crystal silicon.

In step B, a layer of photoresist 1605 is deposited and patterned. This step defines the shape of the structure, such as the torsion beams and the mirror. In step C, the regions in the device layer 1606 as defined by the photoresist is etched with an RIE process. Subsequently in step D, an isotropic etching process (such as HF etching) is performed to remove the unnecessary $SiO_2$ layer and to release the structure. In step E, the mirror and the rest of the structure is coated with reflective metal, such as aluminum, gold, chromium, or silver. After step E, one can dice the wafer into individual chips.

Alternatively, instead of dicing the wafer, one may perform additional RIE on the back side of the wafer to obtain chips with arbitrary shapes. The reason for doing so is that it is difficult to dice non-rectangular shaped chips. Moreover, a circularly shaped chip can fit more easily into a round enclosure which is to be inserted into a pacing lead. Step F shows a photolithography process performed on the back side of the wafer. Step G shows how back side RIE is performed to separate the individual chips.

Assembly of a Fiberoptic Cardiac Wall Motion Timer

Figure 17:
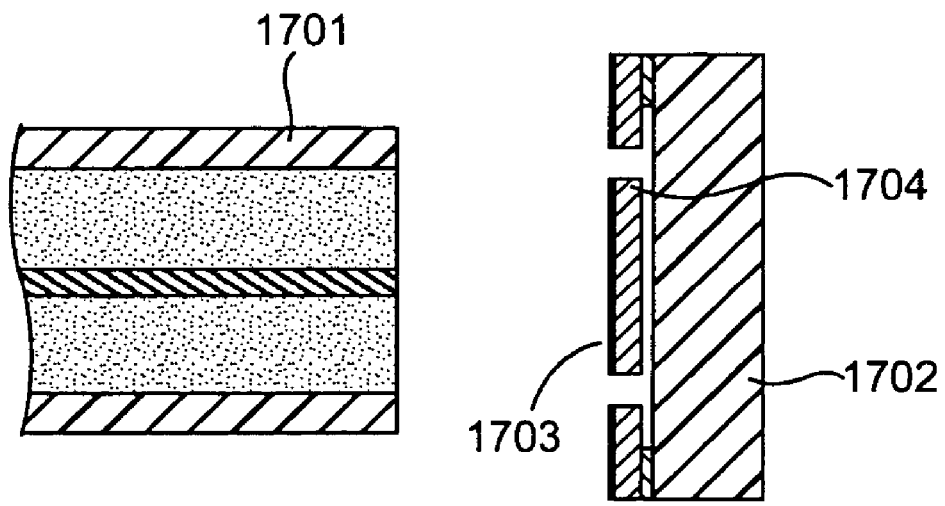
FIG. 17 illustrates an optical fiber aligned in front of a micro-machined mirror in accordance with an embodiment of the present invention.

FIG. 17 illustrates an optical fiber aligned in front of a micro-machined mirror in accordance with an embodiment of the present invention. An optical fiber 1701 is placed in front of chip 1702 which contains mirror 1703. Mirror 1703 is free to rotate around the axis of torsion beam 1704.

Figure 18:
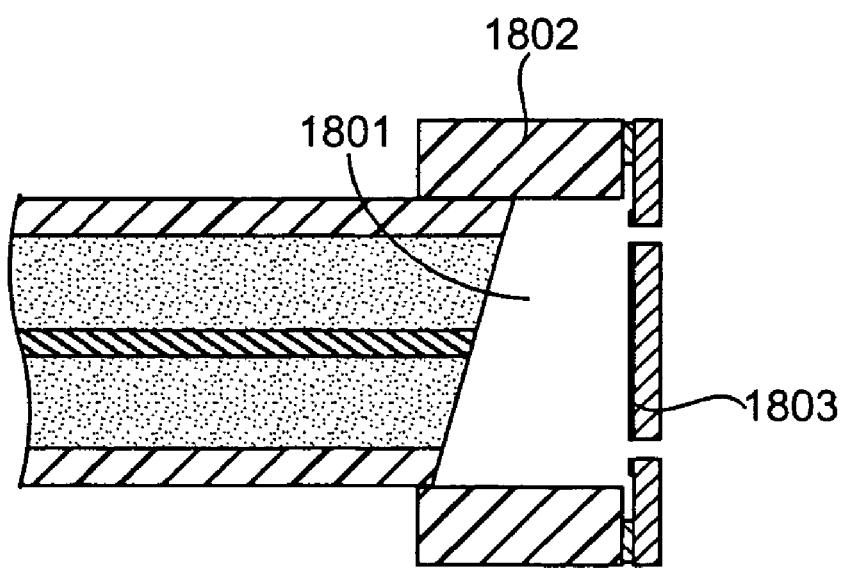
FIG. 18 illustrates an optical fiber situated in a cavity etched in the back of the handle layer of a micro-machined mirror in accordance with an embodiment of the present invention.

FIG. 18 illustrates an optical fiber situated in a cavity etched in the back of the handle layer of a micro-machined mirror in accordance with an embodiment of the present invention. As shown in FIG. 18, a cavity 1801 is etched in a handle layer 1802 of the chip. Ideally, an optical fiber can be directly fitted in cavity 1801 to facilitate alignment of the light. In addition, a reflective layer 1803 is deposited on the back side of the mirror. Note that in this example, the optical fiber is cleaved with an angle to reduce light reflection from the end face of the fiber.

Figure 19:
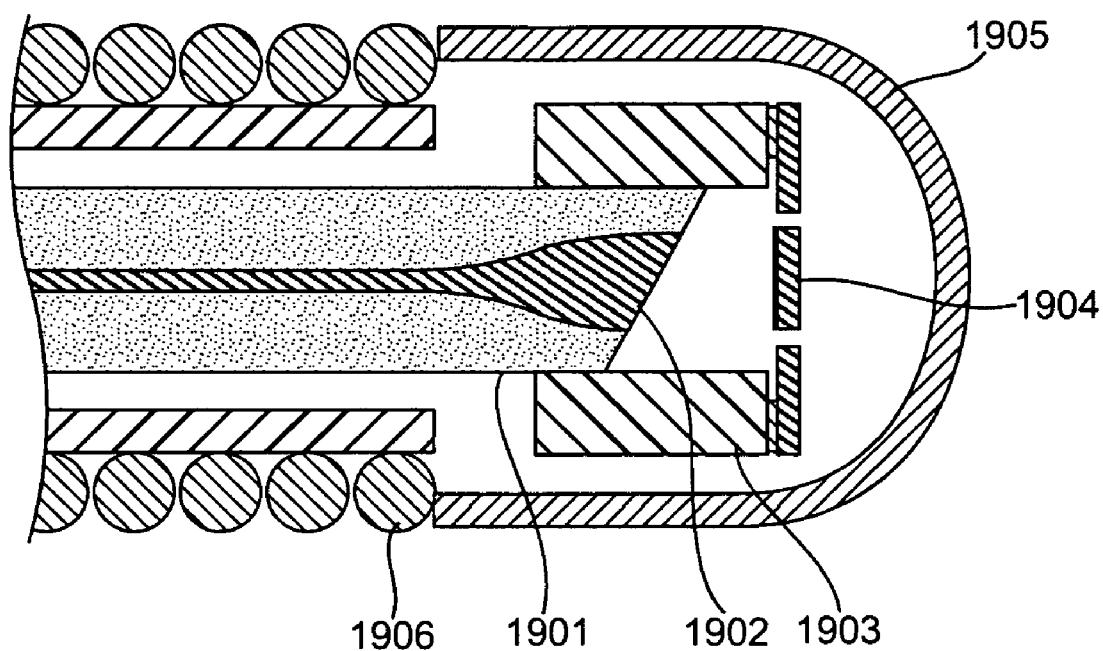
FIG. 19 illustrates an assembly of a fiberoptic cardiac wall motion timer in accordance with an embodiment of the present invention.

FIG. 19 illustrates an assembly of a fiberoptic cardiac wall motion timer in accordance with an embodiment of the present invention. In this example, an optical fiber 1901 with a thermally expanded core 1902 is fitted in a cavity on the back of a sensor chip 1903 which contains mirror 1904. The fiber-mirror assembly resides in a hermetic enclosure 1905. In one embodiment, the outer diameter of enclosure 1905 ranges from about 0.025 to about 0.6 mm. In one embodiment, the outer diameter of enclosure 1905 ranges from about 0.1 to about 0.5 mm. In one embodiment, the outer diameter of enclosure 1905 ranges from about 0.25 to about 0.40 mm. Enclosure 1905 can be made of any convenient material, such as an inert material, which may include stainless steel, platinum, nickel, cobalt, chromium, or an alloy thereof.

Optical fiber 1901 is encased in a metal coil 1906, which is commonly used for cardiac guide wires. A conventional guide wire typically comprises a metal coil and a metal wire in the middle of the coil. In the fiberoptic cardiac wall motion timer shown in FIG. 19, optical fiber 1901 is placed in the middle of metal coil 1906. In one embodiment of the present invention, the outer diameter of coil 1906 ranges from about 0.025 to about 0.6 mm. In one embodiment of the present invention, the outer diameter of coil 1906 ranges from about 0.1 to about 0.5 mm. In one embodiment of the present invention, the outer diameter of coil 1906 ranges from about 0.25 to about 0.40 mm. In addition, the inner diameter of coil 1906 is sufficiently large to fit a standard optical fiber with a diameter of 250 microns. Coil 1906 can be made of any convenient material, such as an inert material, which may include stainless steel, platinum, nickel, cobalt, chromium, or an alloy thereof.

Simultaneous Operation of Multiple Sensors

In certain cases one may want to measure the acceleration of multiple locations within the heart or to measure cardiac motions along different axes. One approach to achieve this goal is to operate multiple fiberoptic cardiac wall motion timers simultaneously with wavelength-division multiplexing (WDM).

Figure 20:
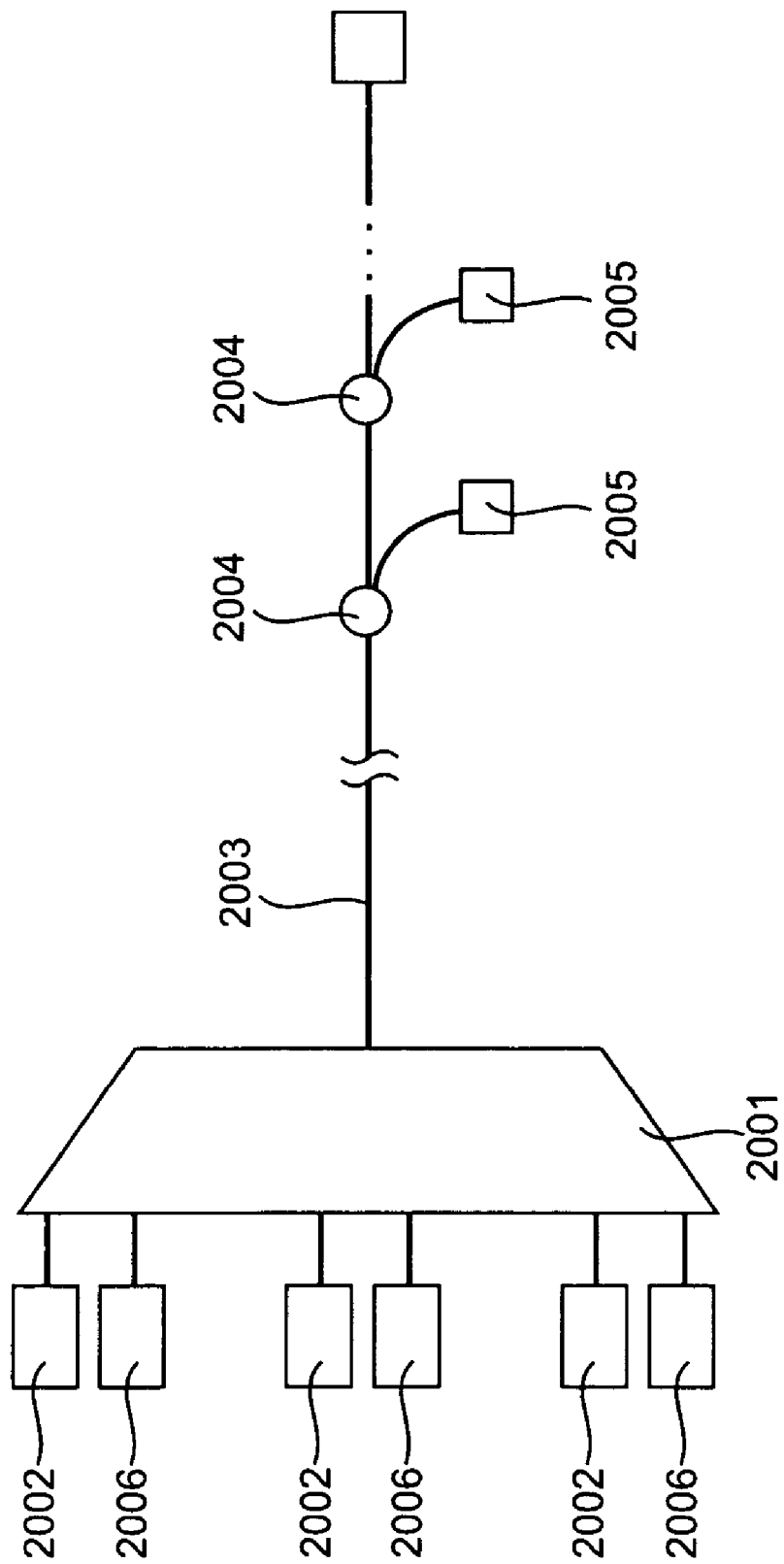
FIG. 20 illustrates a wavelength-division multiplexed configuration of a number of fiberoptic cardiac wall motion timers in accordance with an embodiment of the present invention.

FIG. 20 illustrates a wavelength-division multiplexed configuration of a number of fiberoptic cardiac wall motion timers in accordance with an embodiment of the present invention. As shown in FIG. 20, wavelength-division multiplexer/demultiplexer 2001 couples a number of light sources 2002 and a number of corresponding light detectors 2006 to a main optical fiber 2003. A number of fiberoptic cardiac wall motion timers 2005 are coupled to fiber 2003 through wavelength-selective splitters 2004. In this way, different wavelengths can be transmitted within fiber 2003 and each sensor can operate independently at one given wavelength. Note that wavelength-selective splitter 2004 can be based on different technologies, such as fused biconic taper (FBT), fiber Bragg gating, or thin-film filter. Such a structure may be characterized as a sensor that has a main optical fiber with a number of branch fibers, where each branch fiber includes a transducer at its distal end.

Wavelength-selective splitters 2004 also allow the sensors to transmit reflected light back to main optical fiber 2003. Accordingly, multiplexer/demultiplexer 2001 can demultiplex the reflected light and direct different wavelengths to individual light detectors corresponding to the sensors.

Utility

The subject methods of evaluating tissue location movement find use in a variety of different applications. As indicated above, an important application of the subject invention is for use in cardiac resynchronization, or CRT, also termed biventricular pacing. As is known in the art, CRT remedies the delayed left ventricular mechanics of heart failure patients. In a desynchronized heart, the interventricular septum will often contract ahead of portions of the free wall of the left ventricle. In such a situation, where the time course of ventricular contraction is prolonged, the aggregate amount of work performed by the left ventricle against the intraventricular pressure is substantial. However, the actual work delivered on the body in the form of stroke volume and effective cardiac output is lower than would otherwise be expected. Using the subject approach, the electromechanical delay of the left lateral ventricle can be evaluated and the resultant data employed in CRT, e.g., using the approaches reviewed above and/or known in the art and reviewed at Col. 22, lines 5 to Col. 24, lines 34 of U.S. Pat. No. 6,795,732, the disclosure of which is herein incorporated by reference.

In a fully implantable system the location of the pacing electrodes on multi electrode leads and pacing timing parameters are continuously optimized by the pacemaker. The pacemaker frequently determines the location and parameters which minimizes intraventricular dyssynchrony, interventricular dyssynchrony, or electromechanical delay of the left ventricle lateral wall in order to optimize CRT. This cardiac wall motion sensing system can also be used during the placement procedure of the cardiac leads in order to optimize CRT. An external controller could be connected to the cardiac leads and a skin patch electrode during placement of the leads. The skin patch acts as the reference electrode until the pacemaker is connected to the leads. In this scenario, for example, the optimal left ventricle cardiac vein location for CRT is determined by acutely measuring intraventricular dyssynchrony.

The subject methods and devices can be used to adjust a resynchronization pacemaker either acutely in an open loop fashion or on a nearly continuous basis in a closed loop fashion.

Other uses for this system could be as an ischemia detector. It is well understood that in the event of acute ischemic events one of the first indications of such ischemia is akinesis, i.e., decreased wall motion of the ischemic tissue as the muscle becomes stiffened. A wall motion system would be a very sensitive indicator of an ischemic process, by ratio metrically comparing the local wall motion to a global parameter such as pressure. One can derive important information about unmonitored wall segments and their potential ischemia. For example, if an unmonitored section became ischemic, the monitored segment would have to work harder and have relatively greater motion in order to maintain systemic pressure and therefore ratio metric analysis would reveal that fact.

Another application of such position indicators that record wall motion would be as a potentially superior arrhythmia detection circuit. Current arrhythmia detection circuits rely on electrical activity within the heart. Such algorithms are therefore susceptible to confusing electrical noise for an arrhythmia. There is also the potential for misidentifying or mischaracterizing arrhythmia based on electrical events when mechanical analysis would reveal a different underlying physiologic process. Therefore the current invention could also be adapted to develop a superior arrhythmia detection and categorization algorithm.

Additional applications in which the subject invention finds use include, but are not limited to: the detection of electromechanical dissociation during pacing or arrhythmias, differentiation of hemodynamically significant and insignificant ventricular tachycardias, monitoring of cardiac output, mechanical confirmation of capture or loss of capture for autocapture algorithms, optimization of multi-site pacing for heart failure, rate responsive pacing based on myocardial contractility, detection of syncope, detection or classification of atrial and ventricular tachyarrhythmias, automatic adjustment of sense amplifier sensitivity based on detection of mechanical events, determination of pacemaker mode switching, determining the need for fast and aggressive versus slower and less aggressive anti-tachyarrhythmia therapies, or determining the need to compensate for a weakly beating heart after therapy delivery (where these representative applications are reviewed in greater detail in U.S. Pat. No. 6,795,732, the disclosure of which is herein incorporated by reference), and the like.

In certain embodiments, the subject invention is employed to overcome barriers to advances in the pharmacologic management of CHF, which advances are slowed by the inability to physiologically stratify patients and individually evaluate response to variations in therapy. It is widely accepted that optimal medical therapy for CHF involves the simultaneous administration of several pharmacologic agents. Progress in adding new agents or adjusting the relative doses of existing agents is slowed by the need to rely solely on time-consuming and expensive long-term morbidity and mortality trials. In addition, the presumed homogeneity of clinical trial patient populations may often be erroneous since patients in similar symptomatic categories are often assumed to be physiologically similar. It is desirable to provide implantable systems designed to capture important cardiac performance and patient compliance data so that acute effects of medication regimen variation may be accurately quantified. This may lead to surrogate endpoints valuable in designing improved drug treatment regimens for eventual testing in longer-term randomized morbidity and mortality studies. In addition, quantitative hemodynamic analysis may permit better segregation of drug responders from non-responders thereby allowing therapies with promising effects to be detected, appropriately evaluated and eventually approved for marketing. The present invention allows for the above. In certain embodiments, the present invention is used in conjunction with the Pharma-informatics system, as described in U.S. Provisional Application Ser. No. 60/676,145 filed on Apr. 28, 2005 and U.S. Provisional Application Ser. No. 60/694,078; the disclosures of which are herein incorporated by reference.

Non-cardiac applications will be readily apparent to the skilled artisan, such as, by example, measuring the congestion in the lungs, determining how much fluid is in the brain, assessing distention of the urinary bladder. Other applications also include assessing variable characteristics of many organs of the body such as the stomach. In that case, after someone has taken a meal, the present invention allows measurement of the stomach to determine that this has occurred. Because of the inherently numeric nature of the data from the present invention, these patients can be automatically stimulated to stop eating, in the case of overeating, or encouraged to eat, in the case of anorexia. The present inventive system can also be employed to measure the fluid fill of a patient's legs to assess edema, or other various clinical applications.

Embodiments of the present invention may also be used for orthopedic procedures, wherein the fiberoptic tissue motion sensors can detect how bones are bending or stretching. For example, the present inventive fiber-optical tissue motion sensors that can be used in FES or stimulation of muscles. The advantage herein is that a physician can place a single strand of fiber that runs along the length of a leg and measure various parameters. In other applications, the present inventive sensors can be placed in facial bones for plastic surgical purposes which allow observation of changes in dimension over time.

In other applications, the present inventive sensors can be used for spinal surgery to assist examination of fused parts of the spine and to detect residual motion between fused parts in which case the fusing has to be redone. Additional applications of embodiments of the present invention include use of the subject sensors within or in the vicinity of organs such as bladders, lungs, and stomachs. By placing multiple sensors around the periphery of these organs, a physician can determine the change in their sizes. Embodiments of the present invention allow measurement at multiple points with a single strand of fiber.

Computer Readable Media

One or more aspects of the subject invention may be in the form of computer readable media having programming stored thereon for implementing the subject methods. The computer readable media may be, for example, in the form of a computer disk or CD, a floppy disc, a magnetic "hard card", a server, or any other computer readable media capable of containing data or the like, stored electronically, magnetically, optically or by other means. Accordingly, stored programming embodying steps for carrying-out the subject methods may be transferred or communicated to a processor, e.g., by using a computer network, server, or other interface connection, e.g., the Internet, or other relay means.

More specifically, computer readable medium may include stored programming embodying an algorithm for carrying out the subject methods. Accordingly, such a stored algorithm is configured to, or is otherwise capable of, practicing the subject methods, e.g., by operating an implantable medical device to perform the subject methods. The subject algorithm and associated processor may also be capable of implementing the appropriate adjustment(s).

Of particular interest in certain embodiments are systems loaded with such computer readable mediums such that the systems are configured to practice the subject methods.

Kits

As summarized above, also provided are kits for use in practicing the subject methods. In certain embodiments, the kits at least include a computer readable medium, as described above. The computer readable medium may be a component of other devices or systems, or components thereof, in the kit, such as an adaptor module, a pacemaker, etc. The kits and systems may also include a number of optional components that find use including but not limited to, implantation devices, etc. In addition, the kits may include various systems or components thereof, as described above.

In certain embodiments of the subject kits, the kits will further include instructions for using the subject devices or elements for obtaining the same (e.g., a website URL directing the user to a webpage which provides the instructions), where these instructions are typically printed on a substrate, which substrate may be one or more of: a package insert, the packaging, reagent containers and the like. In the subject kits, the one or more components are present in the same or different containers, as may be convenient or desirable.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. An implantable tissue motion sensor, the tissue motion sensor comprising:
   a light guide having a proximal end and a distal end;
   a mirror located at the distal end, wherein the mirror is configured such that a movement of a tissue located in a subject and stably associated with the mirror causes the mirror to move; and
   a light transmitter and a light detector both optically coupled to the proximal end, wherein the mirror is hinged through a first set of torsion beams to a first frame.

2. The implantable tissue motion sensor according to claim 1, wherein the mirror has a center of mass that is located outside an axis of rotation corresponding to the torsion beams such that motion of a chip containing the mirror in a direction substantially orthogonal to the axis causes the mirror to move.

3. The implantable tissue motion sensor according to claim 1, wherein the first frame is hinged to a second frame through a second set of torsion beams.

4. The implantable tissue motion sensor according to claim 3, wherein said mirror has a center of mass that is located outside both a first axis of rotation corresponding to the first set of torsion beams and a second axis of rotation corresponding to the second set of torsion beams such that motion of a chip containing said mirror in a direction substantially orthogonal to either the first axis or the second axis causes said mirror to move.

5. The implantable tissue motion sensor according to claim 1, wherein the light guide is an optical fiber.

6. The implantable tissue motion sensor according to claim 5, wherein the optical fiber is a single-mode optical fiber.

7. The implantable tissue motion sensor according to claim 5, wherein the optical fiber is a multi-mode optical fiber.

8. The implantable tissue motion sensor according to claim 1, wherein the sensor further comprises a collimating element.

9. The implantable tissue motion sensor according to claim 8, wherein the collimating element is positioned at the distal end of the light guide.

10. The implantable tissue motion sensor according to claim 9, wherein the collimating element is selected from the group consisting of a convex lens, a piano-convex lens, and a graded index (GRIN) lens.

11. The implantable tissue motion sensor according to claim 8, wherein said collimating element is integral with said distal end of said light guide.

12. The implantable tissue motion sensor according to claim 11, wherein said collimating element comprises an expanded core of said light guide.

13. The implantable tissue motion sensor according to claim 1, wherein the distal end of the light guide and the mirror are present in an elongated structure that is dimensioned to be placed within a vascular lead.

14. The implantable tissue motion sensor according to claim 13, wherein the vascular lead is a cardiac pacing lead.

15. The implantable tissue motion sensor according to claim 13, wherein the elongated structure comprises a metal coil.

16. The implantable tissue motion sensor according to claim 13, wherein a distal end of the elongated structure is hermetically sealed.

17. The implantable tissue motion sensor according to claim 1, wherein the light guide comprises a main optical fiber and two or more branch fibers, wherein a distal end of each of the two or more branch fibers comprises a respective mirror.

18. The implantable tissue motion sensor according to claim 17, wherein each of the branch fibers is coupled to the main optical fiber through a wavelength-selective mechanism.

19. The implantable tissue motion sensor according to claim 18, wherein the wavelength-selective mechanism is selected from the group consisting of a fused bionic taper (FBT), a fiber Bragg grating and a thin film-based filter.

20. The implantable tissue motion sensor according to claim 17, wherein the sensor further comprises a wavelength-division multiplexer/demultiplexer coupled to the main optical fiber.

21. A system for evaluating movement of a tissue location, the system comprising:

(a) an implantable tissue motion sensor, comprising:

a light guide having a proximal end and a distal end;

a mirror located at the distal end, wherein the mirror is configured such that a movement of a tissue located within a subject and stably associated with the mirror causes the mirror to move; and a light transmitter and a light detector both optically coupled to the proximal end; and (b) a signal processing element configured to employ a signal obtained from the implantable tissue motion sensor that is induced by the movement of the tissue to evaluate the movement of the tissue, wherein the mirror is hinged through a first set of torsion beams to a first frame.

22. A device for evaluating movement of a tissue location in a subject, the device comprising:

(a) an implantable tissue motion sensor comprising:

a light guide having a proximal end and a distal end;

a mirror located at the distal end and stably associated with the tissue location, wherein the movement of the tissue location causes the mirror to move; and a light transmitter and a light detector both optically coupled to the proximal end; and (b) a signal processing element configured to employ a signal obtained from the implantable tissue motion sensor that is induced by the movement of the tissue location to evaluate the movement of the tissue location, wherein the reflective element comprises a micro-machined chip with a mirror having at least one reflective surface, the mirror connected to a first frame of the micro-machined chip by one or more torsional beams.

* * * * *